United States Patent
Vemula et al.

(10) Patent No.: US 12,202,841 B2
(45) Date of Patent: Jan. 21, 2025

(54) THERAPEUTIC AGENTS FOR ENHANCING EPITHELIAL AND/OR ENDOTHELIAL BARRIER FUNCTION

(71) Applicants: ARTUS THERAPEUTICS, INC., Allston, MA (US); INSTITUTE FOR STEM CELL SCIENCE AND REGENERATIVE MEDICINE, Bangalore (IN)

(72) Inventors: Praveen Kumar Vemula, Bangalore (IN); Nicholas Kenneth Terrett, Allston, MA (US); Sakthimala Jagadeesan, Allston, MA (US); Venkatesh Ravula, Bangalore (IN)

(73) Assignees: ARTUS THERAPEUTICS, INC., Allson, MA (US); INSTITUTE FOR STEM CELL SCIENCE AND REGENERATIVE MEDICINE, Banaglore (IN)

( * ) Notice: Subject to any disclaimer, the term of this patent is extended or adjusted under 35 U.S.C. 154(b) by 0 days.

(21) Appl. No.: 18/428,542

(22) Filed: Jan. 31, 2024

(65) Prior Publication Data
US 2024/0239809 A1   Jul. 18, 2024

Related U.S. Application Data

(63) Continuation of application No. PCT/US2023/077699, filed on Oct. 25, 2023.

(60) Provisional application No. 63/419,015, filed on Oct. 25, 2022.

(51) Int. Cl.
| | |
|---|---|
| C07D 498/04 | (2006.01) |
| A61K 9/00 | (2006.01) |
| A61K 31/352 | (2006.01) |
| A61K 31/519 | (2006.01) |
| A61P 1/04 | (2006.01) |
| C07D 311/02 | (2006.01) |

(52) U.S. Cl.
CPC .......... *C07D 498/04* (2013.01); *A61K 9/0053* (2013.01); *A61K 31/352* (2013.01); *A61K 31/519* (2013.01); *A61P 1/04* (2018.01); *C07D 311/02* (2013.01)

(58) Field of Classification Search
CPC .............. C07D 498/04; C07D 311/102; A61K 31/352; A61K 31/519; A61P 1/04
See application file for complete search history.

(56) References Cited

U.S. PATENT DOCUMENTS

| | | |
|---|---|---|
| 3,987,186 A | 10/1976 | Devlin et al. |
| 9,994,542 B2 | 6/2018 | Rinsch et al. |
| 2004/0225013 A1 | 11/2004 | Strobel et al. |
| 2010/0210680 A1 | 8/2010 | Grove et al. |
| 2013/0310576 A1 | 11/2013 | Kudou et al. |
| 2021/0267932 A1 | 9/2021 | Jala et al. |
| 2022/0106284 A1 | 4/2022 | Grenning et al. |

FOREIGN PATENT DOCUMENTS

WO   WO 2004/073612 A2   9/2004

OTHER PUBLICATIONS

Pubchem, SID 236731649, Modify Date: Feb. 13, 2015., Retrieved from the Internet <URL: https://pubchem.ncbi.nlm.nih.gov/ substance/ 236731649> entire document.
Pubchem, SID 111133, Modify Date: Dec. 19, 2011., Retrieved from the Internet <URL: https://pubchem.ncbi.nlm.nih.gov/ substance/ 111133> entire document.
International Search Report issued in International Application No. PCT/US2023/077699, dated Mar. 6, 2024, 12 pages.
Singh, et al., "Enhancement of the gut barrier integrity by a microbial metabolite through the Nrf2 pathway", Nature Communications (2019), https://doi.org/10.1038/s41467-018-07859-7.

*Primary Examiner* — Kevin E Weddington
(74) *Attorney, Agent, or Firm* — Morgan, Lewis & Bockius LLP

(57) ABSTRACT

The present invention relates to novel compounds and compositions thereof. The compositions are useful in the treatment of an epithelial or endothelial barrier dysfunction disorder in a subject.

23 Claims, 11 Drawing Sheets

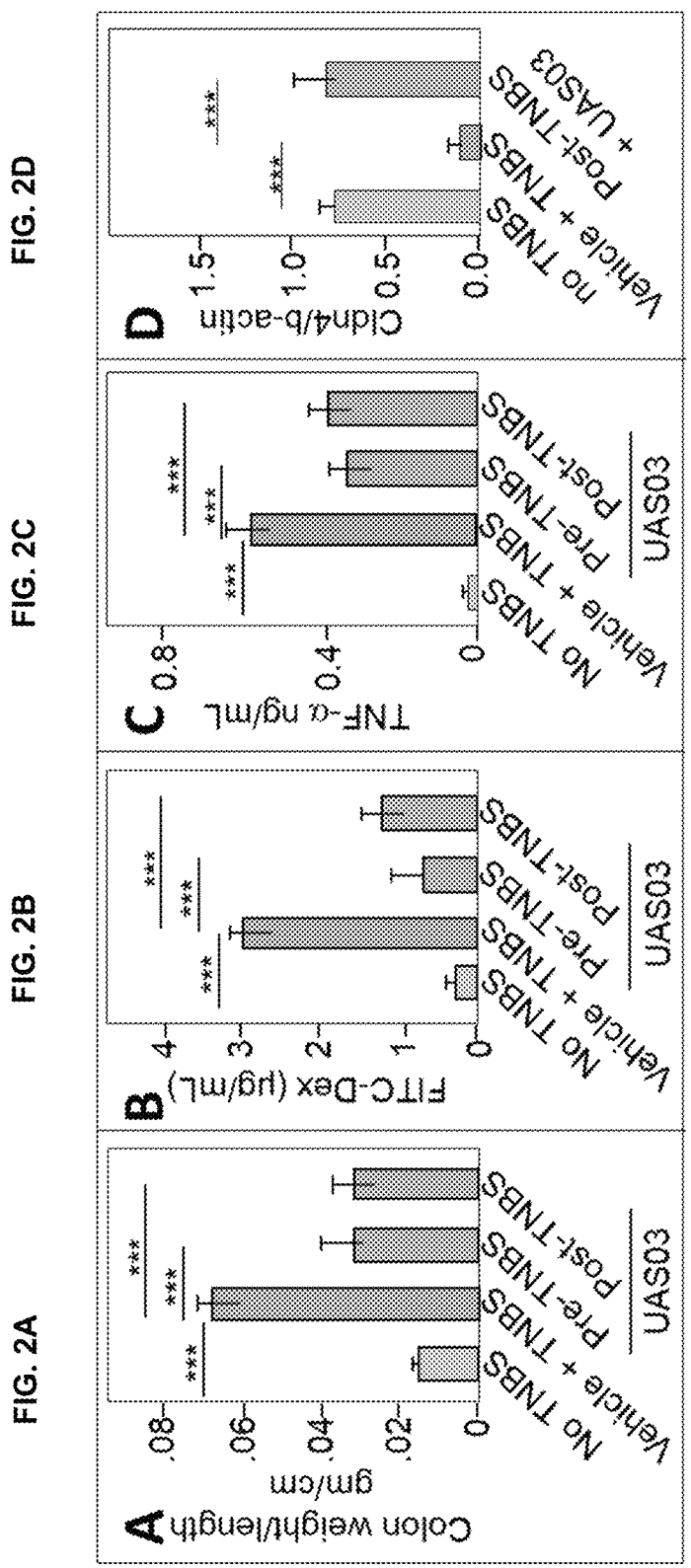

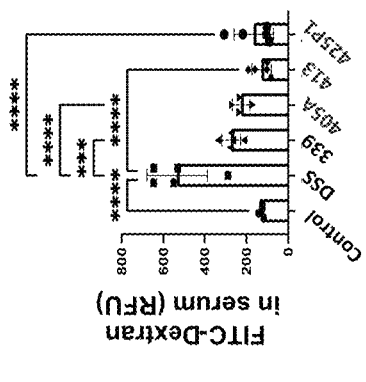
FIG. 6A
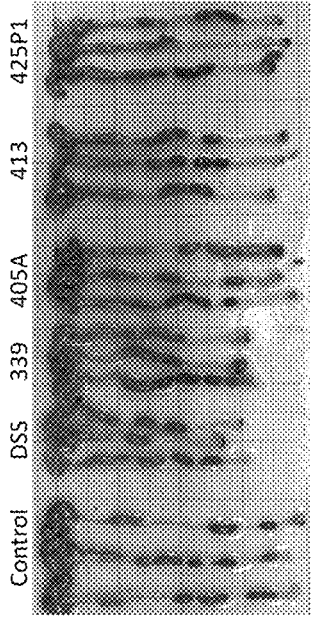
FIG. 6B
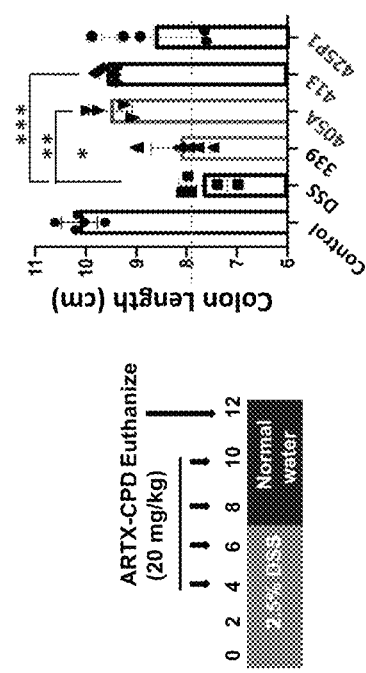
FIG. 6C
FIG. 6D
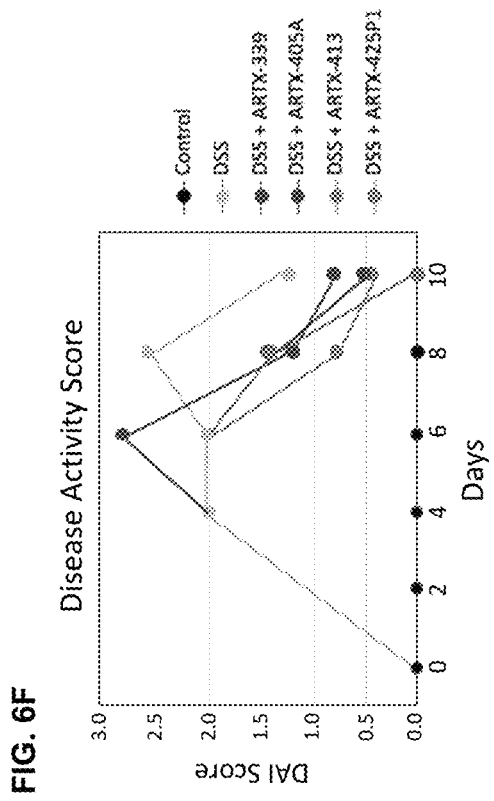
FIG. 6E
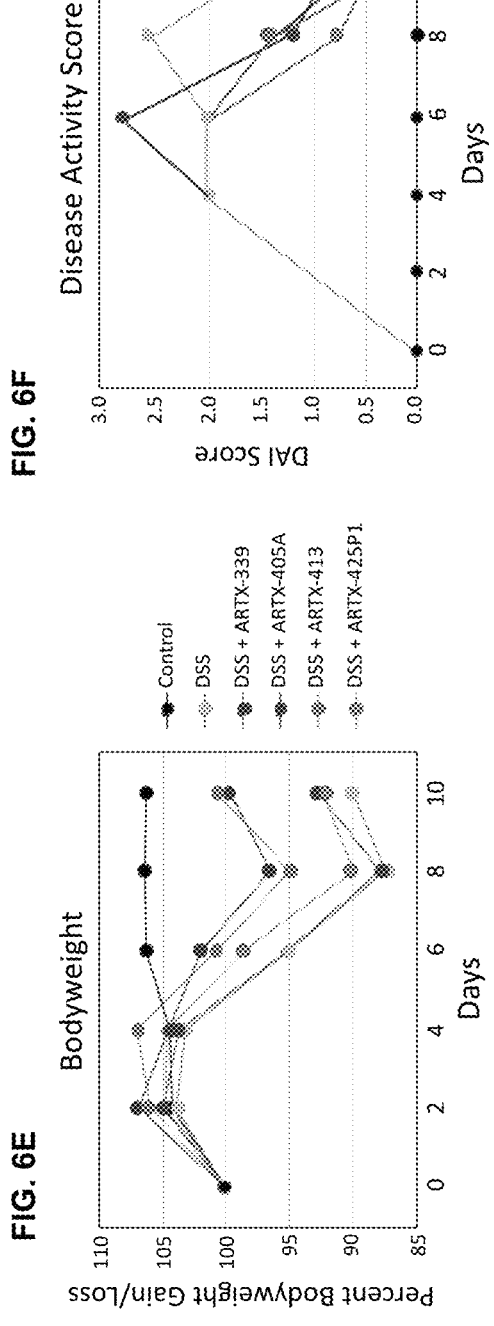
FIG. 6F

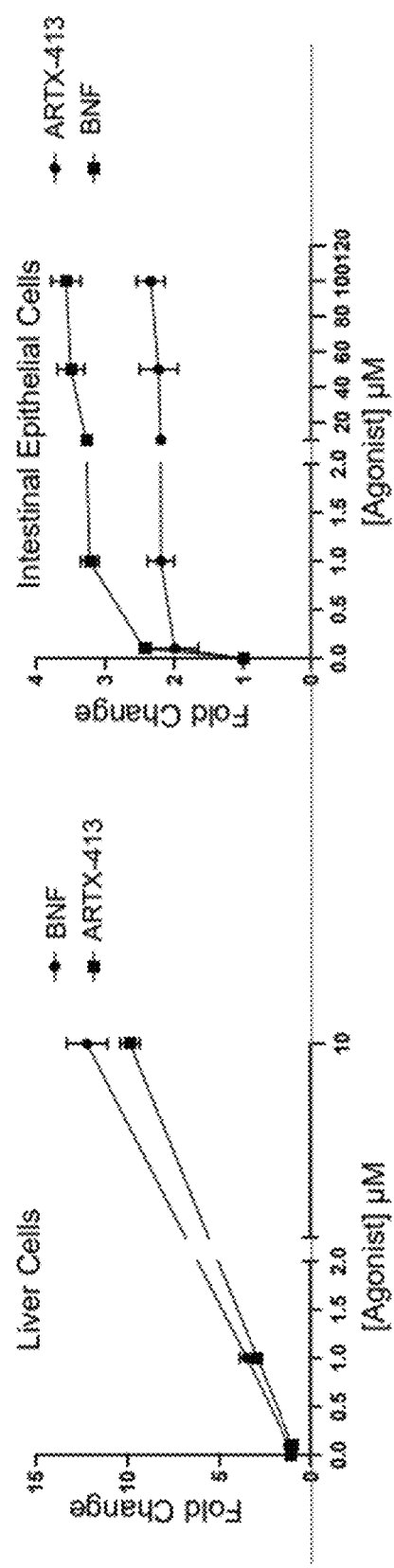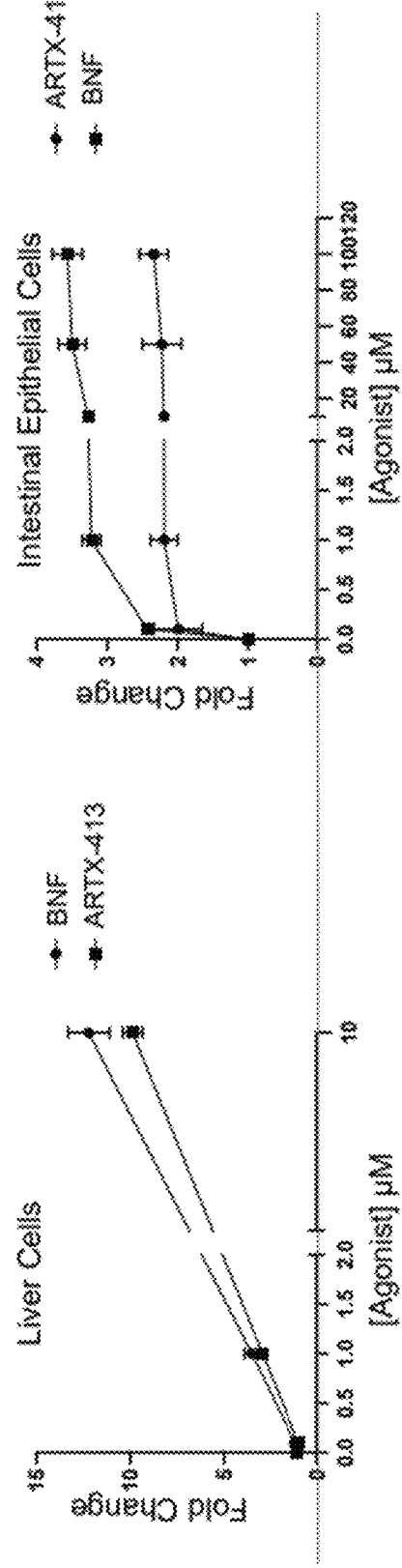
FIG. 7A
FIG. 7B

| Cell Number | File Name | hERG Current Inhibition (%) | | | | | |
|---|---|---|---|---|---|---|---|
| | | 0.3 µM | 1 µM | 3 µM | 10 µM | 30 µM |
| Cell 1 | 20220614_1_1 | -0.38 | -0.53 | -1.73 | -1.07 | 4.83 |
| Cell 2 | 20220614_1_3 | 1.02 | 4.69 | 6.05 | NA | NA |
| Cell 3 | 20220614_1_4 | -0.76 | -1.59 | -2.17 | -1.57 | 0.98 |
| Cell 4 | 20220614_1_5 | NA | NA | NA | -0.05 | 4.87 |
| Average inhibition (%) | | -0.04 | 0.86 | 0.72 | 0.89 | 3.56 |
| SD | NA | 0.94 | 3.37 | 4.63 | 0.77 | 2.24 |
| SEM | NA | 0.54 | 1.94 | 2.67 | 0.45 | 1.29 |

THERAPEUTIC AGENTS FOR ENHANCING EPITHELIAL AND/OR ENDOTHELIAL BARRIER FUNCTION

PRIORITY

This Application is a continuation of International Application PCT/US23/77699, filed Oct. 25, 2023, which claims the benefit of, and claims priority to, U.S. Provisional Application No. 63/419,015 filed Oct. 25, 2022, each of which is hereby incorporated by reference in its entirety.

BACKGROUND OF THE INVENTION

Barrier dysfunction (epithelial or endothelial) is observed in numerous medical disorders and conditions. For example, the breakdown of normal epithelial or endothelial barrier function is a common feature of many chronic autoimmune diseases and inflammatory diseases, as well as other metabolic and neuronal disorders. In epithelial layers such as the intestinal epithelium, barriers between cells consist of tight junction complexes formed by tight junction proteins such as claudins and occludins. In endothelial cell layers such as in blood vessels and the heart, barriers between cells consist of both tight and adherens junctions formed by tight junction proteins and vascular endothelium (VE) cadherin, respectively. Maintaining strong physical barriers in epithelial and endothelial layers is important in maintaining immune homeostasis.

Damage to intestinal barrier function results in the translocation of microbes and microbial antigens into the systemic circulation, leading to hyperinflammation and organ-specific immune dysfunction. Intestinal barrier dysfunction is associated with a variety of diseases including but not limited to Inflammatory Bowel Disease (IBD), irritable bowel syndrome (IBS), and celiac disease (CeD). Gut barrier dysfunction is also strongly correlated with other autoimmune, inflammatory, and metabolic diseases including but not limited to obesity, alcoholic and non-alcoholic liver disease, atherosclerosis, heart failure, hypertension, food allergies, as well as cancer. It has been reported that various external factors like alcohol, nonsteroidal anti-inflammatory drugs (NSAID), and specific pathogens can directly alter gut barrier function contributing to the pathogenesis of various diseases. The imbalance of microbes in the gut (microbial dysbiosis) has been also linked with gut barrier dysfunction and an immature immune system leading to wide spectrum of intestinal, hepatic and neurological disorders.

Further, the vascular physical barrier includes a monolayer of endothelial cells interconnected by tight junction protein complexes and VE cadherin. Acute respiratory distress syndrome (ARDS), an example of an endothelial dysfunction disease, is characterized by a breakdown of the paracellular barriers between vascular endothelial cells in alveolar capillaries as well as between alveolar epithelial cells, thereby allowing the seepage of fluids and immune cells into the lungs.

Ulcerative colitis (UC) and Crohn's disease (CD), collectively referred to as Inflammatory Bowel Disease (IBD), affect 3 million Americans. Intestinal barrier hyperpermeability is a key factor in the pathogenesis and progression of disease in IBD patients. Hyperpermeability is caused in part by altered expression and/or distribution of tight junction proteins (TJPs) between cells. Changes in the expression and distribution of TJPs have been shown in clinically active IBD patients and enhancing barrier integrity is associated with clinical remission and improved patient outcome. More broadly, intestinal hyperpermeability is associated with an increased risk of relapse, has been reported both in clinically active and inactive IBD patients, and correlates with disease severity. In addition, treatments that improve barrier integrity prevent the progression of IBD in animal models. Further, patients with Crohn's disease or UC that exhibit high levels of intestinal permeability have a poorer prognosis than patients with relatively low levels of intestinal permeability. Similarly, disease risk is greater in healthy relatives of Crohn's disease patients who exhibit increased intestinal permeability.

Despite mounting evidence of the prominent role that barrier dysfunction plays in IBD, current FDA-approved IBD therapeutics and most therapeutics in development target intestinal inflammation and do not directly affect (i.e., target) barrier dysfunction. Primary goals of IBD therapies are to prevent progression from milder to more severe forms of the disease, induce remission of acute flares, and/or maintain remission. Unfortunately, up to 50 to 60% of UC patients fail mesalamine (5-aminosalicylic acid; 5ASA) treatment, the first-line therapeutic for UC patients with mild to moderate disease. For the ~50% of UC patients who fail mesalamine, corticosteroids and then off-label use of immunosuppressants such as 6-mercaptopurine are the next line of treatment. The first-line therapies for CD patients are typically corticosteroids. Biologics that target TNF-α and integrin $\alpha_4\beta_7$ have become the standard of care for moderate to severe UC and CD patients who do not respond to "conventional" immunosuppressant therapies. The anti-integrin biologics may be less toxic than TNF-α mAbs, but drawbacks of both TNF-α and integrin $\alpha_4\beta_7$ mAbs include lack of oral availability, relatively low response rates of 45 to 60%, development of resistance, and irreversibility.

There is a need for therapeutic agents that directly target barrier dysfunction and enhance barrier integrity to promote mucosal or tissue healing. Of particular need is an oral, non-toxic, non-immunosuppressive therapeutic that directly enhances the re-establishment of epithelial integrity and maintains long-term remission in IBD. The present invention meets these and other needs.

SUMMARY OF THE INVENTION

In the various aspects and embodiments, this disclosure provides compounds (i.e., active pharmaceutical agents) that ameliorate epithelial and/or endothelial barrier dysfunction, and therefore are useful for treating various diseases and conditions in which tissue barrier dysfunction is involved. Exemplary conditions include those involving gastrointestinal inflammation and/or permeability, including Inflammatory Bowel Disease (IBD) (i.e., Ulcerative Colitis or Crohn's Disease) as well as other diseases of the gastrointestinal tract and diseases involving inflammation or tissue permeability of other tissues and organs. This disclosure further provides pharmaceutical compositions comprising the compounds as well as methods of treatment and use in therapy.

In various aspects and embodiments, the present invention provides novel compounds of Formula (I), Formula (II), and Formula (III) and compositions thereof as described in detail herein. In some embodiments, the compounds described herein exhibit gastric and/or intestinal stability, thereby enhancing their efficacy as an oral therapeutic, as well as enhancing their use in therapy with other routes of administration. In some embodiments, the compounds described herein exhibit low risk of toxicity with long term use (e.g., low risk of genotoxicity or toxicity associated with quinone formation).

In various embodiments, the present disclosure provides a compound of Formula (I) or a pharmaceutically acceptable salt thereof.

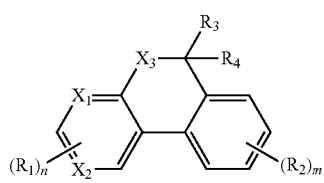

(I)

According to Formula (I):
each $R_1$ is independently selected from the group consisting of OH, $NO_2$, Halo, $CF_3$, $NR_3R_4$, $(C_1-C_6)$alkoxy, —C(O) $(C_1-C_6)$alkyl, and —C(O)O$(C_1-C_6)$alkyl;
each $R_2$ is a substituent other than OH;
$R_3$ and $R_4$ each is independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo;
$X_1$ and $X_2$ are each independently C or N, with proviso that $X_1$ and $X_2$ cannot both be C;
$X_3$ is O or S;
m is an integer in the range of 1 to 4; and
n is an integer in the range of 1 to 4.

In various embodiments, the present disclosure provides a compound of Formula (II) or a pharmaceutically acceptable salt thereof.

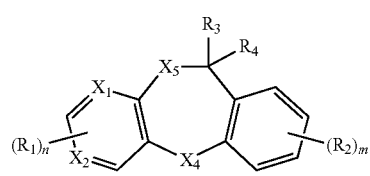

(II)

According to Formula (II):
each $R_1$ is independently selected from the group consisting of OH, $NO_2$, Halo, $CF_3$, $NR_3R_4$, $(C_1-C_6)$alkoxy, —C(O) $(C_1-C_6)$alkyl, and —C(O)O$(C_1-C_6)$alkyl;
each $R_2$ is a substituent other than OH;
$R_3$ and $R_4$ are each independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo;
$X_1$ and $X_2$ are independently C or N;
$X_4$ and $X_5$ are either both a bond, or $X_4$ is CR $R_6$ and $X_5$ is S, O, or $CR_7R_8$;
$R_5$, $R_6$, $R_7$, and $R_8$ are each independently selected from the group consisting of H, Halo, alkyl, alkenyl, and alkoxy;
m is an integer in the range of 1 to 4; and
n is an integer in the range of 1 to 4.

In various embodiments, the present disclosure provides a compound of Formula (III) or a pharmaceutically acceptable salt thereof.

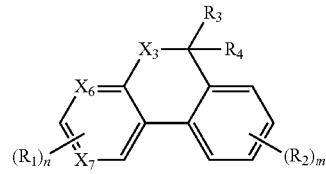

(III)

According to Formula (III):
each $R_1$ is independently selected from the group consisting of OH, $NO_2$, Halo, $CF_3$, $NR_3R_4$, $(C_1-C_6)$alkoxy, —C(O) $(C_1-C_6)$alkyl, and —C(O)O$(C_1-C_6)$alkyl;
each $R_2$ is a substituent other than OH;
$R_3$ and $R_4$ are each independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo; with proviso that $R_3$ and $R_4$ cannot both be H;
$X_6$ and $X_7$ are each independently C or N;
$X_3$ is O or S;
m is an integer in the range of 1 to 4; and
n is an integer in the range of 1 to 4.

In various embodiments, the compounds of Formula (I), (II) or (III) are activators/ligands of the aryl hydrocarbon receptor (AhR). In various embodiments, the compounds of Formula (I), (II) or (III) are non-genotoxic, even with long term use. In various embodiments, the compounds of Formula (I), (II) or (III) do not show significant or substantial quinone formation. In various embodiments, the compounds of Formula (I), (II) or (III) are effective for enhancing the barrier integrity of epithelial and endothelial tissues, including in some embodiments the barrier function of the gastrointestinal tract (e.g., the small intestine and/or large intestine).

In other aspects, the present disclosure provides a pharmaceutical composition comprising a compound of Formula (I), (II), or (III) or a pharmaceutically acceptable salt or solvate thereof, and a pharmaceutically acceptable excipient and/or carrier.

In various embodiments, the composition is formulated for oral delivery to the gastrointestinal tract. Alternatively, the composition is formulated for delivery directly to the lung, or for parenteral delivery, including for example by a route selected from intravenous, intraarterial, intramuscular, intradermal, intrathecal, and subcutaneous administration. Other forms of administration, including for topical or local administration to target tissues (including, for example, the eyes, ears, or any mucosal surface, or the skin), are contemplated by this disclosure.

In other aspects, the present disclosure provides methods for treating an epithelial or endothelial dysfunction disorder in a subject. The method comprises administering to a subject the compound of Formula (I), (II), or (III) or a pharmaceutically acceptable salt thereof, or the pharmaceutical composition thereof. In embodiments, the method induces the expression of tight junction proteins in a tissue. In exemplary embodiments, the subject has inflammation to be treated of one or more organs or tissues selected from liver, kidneys, pancreas, heart, lungs, skin, muscle, fat, brain, eyes, bone, marrow, intestine, cartilage, and skin. Such inflammation can be mitigated through systemic or local treatment with the compounds and compositions, or by treatment of gut barrier function.

Other aspects and embodiments of the disclosure will be apparent from the following Figures and Detailed Description.

BRIEF DESCRIPTION OF THE FIGURES

The foregoing summary, as well as the following detailed description of the invention, will be better understood when read in conjunction with the appended drawings.

FIGS. 2A-D illustrates that UAS03 is efficacious in a mouse 2,4,6-trinitrobenzenesulfonic acid (TNBS) model when administered either pre- or post-TNBS treatment. Pre-treatment: Mice (n=10 per group) were given UAS03 orally QD (20 mg/kg) for 7 days followed by administration of TNBS. Mice were euthanized 72 h post-TNBS treatment. Post-treatment: Mice (n=10 per group) received UAS03 QD (20 mg/kg) 24, 48, and 72 h post-TNBS. A) Ratio of colon weight/length. B) Intestinal permeability evaluated using a FITC-dextran leakage assay. C) Serum levels of TNF-α measured using a standard ELISA method. D) Claudin-4 (Cldn4) expression in mouse colons. Panel D shows data from a separate experiment than the other panels. Error bars, ±SEM; ***p<0.001.

FIG. 3A. Quinone formation by UAS03. FIG. 3B. Quinones can form toxic reactive oxygen radicals, or conjugate with proteins containing reactive thiols leading to potential long-term toxicity.

FIGS. 6A-F illustrate efficacy of ARTX-339, ARTX-405A, ARTX-413, and ARTX-425P1 in the murine DSS model of ulcerative colitis. A. $C_{57}BL/6$ mice (7-8-week old mice) were supplied with 2.5% DSS in their drinking water for 7 days. Starting on day 4 post DSS treatment, mice were dosed once every other day with 100 µL vehicle (0.25% sodium carboxymethylcellulose used in the formulation of ARTX compounds), or 100 µL ARTX-339, ARTX-405A, ARTX-413, or ARTX-425P1 at 20 mg/kg body weight by oral gavage on days 4, 6, 8, and 10. Mice were euthanized on day 12. FITC dextran was administered to the mice via oral gavage 4 hours preceding euthanization. Following euthanization, colons were dissected, and their length measured. B. Measurements of colon length. C. Photographs of dissected colons. D. Measurement of FITC-dextran in serum following euthanization. FITC-dextran, a large fluorescent molecule, is normally at least partially blocked from entering the blood stream by the intestinal epithelial layer. Higher levels of serum FITC-dextran following DSS-treatment is an indication of a loss of barrier function. E. Body weight was measured every other day starting at day 0 with the initiation of DSS treatment. F. Disease activity index (DAI) scores were assigned every other day. The higher the DAI score, the worse the symptoms. ** indicates p<0.0001; * indicates p<0.001; ** indicates=p<0.01.

FIGS. 7A-B illustrates the ability of ARTX-413 to activate the AhR signaling pathway.

DETAILED DESCRIPTION OF THE INVENTION

Figure 1:
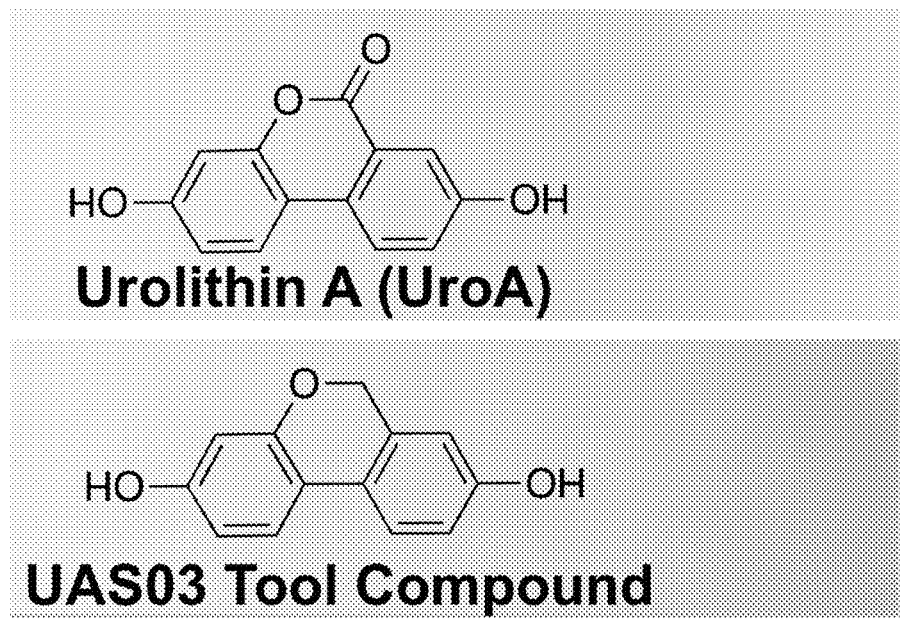
FIG. 1 illustrates the chemical structures of Urolithin A (UroA) and UAS03.

In the various aspects and embodiments, this disclosure provides compounds that reduce epithelial and/or endothelial barrier dysfunction, and therefore are useful for treating various diseases and conditions in which tissue barrier dysfunction is involved. Exemplary conditions include those involving gastrointestinal inflammation and/or permeability, including Inflammatory Bowel Disease (IBD) (i.e., Ulcerative Colitis or Crohn's Disease) as well as other diseases of the gastrointestinal tract and diseases involving other tissues and organs. Accordingly, the active agents described herein find use for treating, ameliorating, or preventing conditions such as alcohol associated liver disease (AALD), alcoholic fatty liver disease, non-alcoholic fatty liver disease, chronic kidney disease, sepsis and other systemic inflammatory diseases, autoimmune diseases, metabolic diseases, and neuroinflammatory and neurodegenerative diseases, among others. This disclosure further provides pharmaceutical compositions comprising the compounds as well as methods of treatment or use in therapy.

In various aspects and embodiments, the present invention provides novel compounds of Formula (I), Formula (II), and Formula (III) and compositions thereof as described in detail herein. In some embodiments, the compounds described herein exhibit gastric and/or intestinal stability, thereby enhancing their efficacy as an oral therapeutic. In some embodiments, the compounds described herein exhibit low risk of toxicity with long term use (e.g., low risk of genotoxicity or toxicity associated with quinone formation).

In various embodiments, the present disclosure provides a compound of Formula (I) or a pharmaceutically acceptable salt thereof.

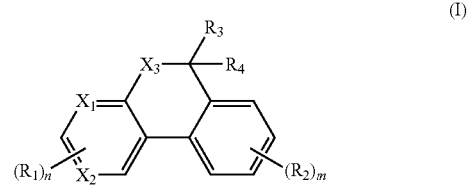

According to Formula (I):
each $R_1$ is independently selected from the group consisting of OH, $NO_2$, Halo, $CF_3$, $NR_3R_4$, $(C_1-C_6)$alkoxy, —C(O) $(C_1-C_6)$alkyl, and —C(O)O$(C_1-C_6)$alkyl;
each $R_2$ is a substituent other than OH;
$R_3$ and $R_4$ each is independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo;
$X_1$ and $X_2$ are each independently C or N, with proviso that $X_1$ and $X_2$ cannot both be C;
$X_3$ is O or S;
m is an integer in the range of 1 to 4; and
n is an integer in the range of 1 to 4.

Without intending to be bound by theory, it is believed that by avoiding hydroxyl at $R_2$ and replacing at least one of $X_1$ and $X_2$ with N, the compound can have the effect of reducing overall reactivity at $R_1$ and $R_2$. In some embodiments, $X_1$ and $X_2$ are each N.

In various embodiments, each $R_2$ is independently selected from the group consisting of Halo, $NO_2$, $CF_3$, $NR_3R_4$, $(C_1-C_6)$alkoxy, —C(O) $(C_1-C_6)$alkyl, $(C_3-C_8)$cycloalkyl, and —C(O)O$(C_1-C_6)$alkyl. In some embodiments, $R_2$ is Halo, and m is 1 or 2. For example, $R_2$ can be selected from F, Cl, Br, and I. In some embodiments, one or more of $R_2$ is methyl, ethyl, methoxy, or isopropyl.

In some embodiments, $X_3$ is O.
In some embodiments, $R_1$ is OH, and n is 1 or 2.
In certain embodiments, $R_3$ and $R_4$ are each H or a $C_1$ to $C_3$ alkyl, and which is optionally methyl, ethyl or isopropyl. In some embodiments, substituents at R3 and/or R4 are sufficiently bulky to reduce interactions of the compound with DNA (e.g., reduce DNA intercalation). In certain embodiments, one of $R_3$ and $R_4$ is $(C_1-C_6)$ alkyl or $(C_1-C_6)$ alkenyl, and the other is H. In certain embodiments, $R_3$ and $R_4$ are each H. In still other embodiments, $R_3$ and $R_4$ together with the carbon to which they are attached form a $(C_3-C_8)$ cycloalkyl or $(C_3-C_8)$ heterocyclo.

In various embodiments of Formula (I), $R_1$ is OH and n is 1; $R_2$ is Halo and m is 1; $X_1$ and $X_2$ are both N; $X_3$ is O; and $R_3$ and $R_4$ are each H.

In one embodiment, the compound of Formula (I) has the structure:

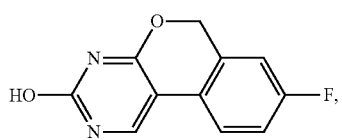

also referred to herein as ARTX-413.

Thus, in one embodiment, the compound of Formula (I) is 8-fluoro-6H-isochromeno[3,4-d]pyrimidin-3-ol.

In one embodiment, the compound of Formula (I) has the structure:

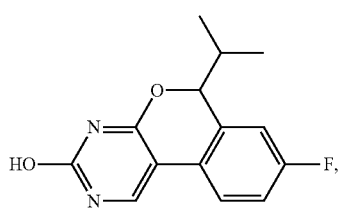

also referred to herein as ARTX-436. Thus, in one embodiment, the compound of Formula (I) is 8-fluoro-6-isopropyl-6H-isochromeno[3,4-d]pyrimidin-3-ol.

In one embodiment, the compound of Formula (I) has the structure:

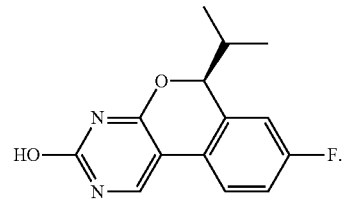

Thus, in one embodiment, the compound of Formula (I) is (S)-8-fluoro-6-isopropyl-6H-isochromeno[3,4-d]pyrimidin-3-ol.

In one embodiment, the compound of Formula (I) has the structure:

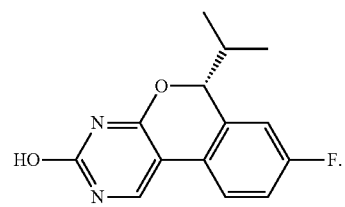 [SMILES: CC(C)C1Oc2nc(O)ncc2-c2ccc(F)cc21]

Thus, the compound of Formula (I) may be (R)-8-fluoro-6-isopropyl-6H-isochromeno[3,4-d]pyrimidin-3-ol.

In various embodiments, the present disclosure provides a compound of Formula (II) or a pharmaceutically acceptable salt thereof.

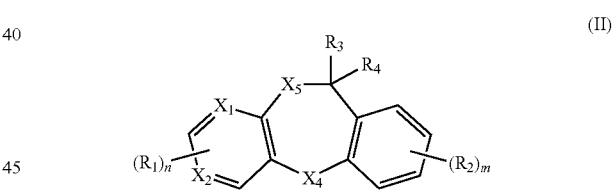

(II)

According to Formula (II):
each $R_1$ is independently selected from the group consisting of OH, $NO_2$, Halo, $CF_3$, $NR_3R_4$, $(C_1-C_6)$alkoxy, —C(O) $(C_1-C_6)$alkyl, and —C(O)O$(C_1-C_6)$alkyl;
each $R_2$ is a substituent other than OH;
$R_3$ and $R_4$ are each independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo;
$X_1$ and $X_2$ are independently C or N;
$X_4$ and $X_5$ are either both a bond, or $X_4$ is $CR_5R_6$ and $X_5$ is S, O, or $CR_7R_8$;
$R_5$, $R_6$, $R_7$, and $R_8$ are each independently selected from the group consisting of H, Halo, alkyl, alkenyl, and alkoxy;
m is an integer in the range of 1 to 4; and
n is an integer in the range of 1 to 4.

Without intending to be bound by theory, it is believed that by incorporating a five or seven membered ring as shown in Formula (II), the molecule will be substantially less planar, and avoid genotoxicity associated with DNA intercalation.

In some embodiments, each $R_1$ is OH, and n is 1 or 2.

In some embodiments, both $X_4$ and $X_5$ are a bond.

In some embodiments, $X_4$ is $CH_2$.

In some embodiments, $X_4$ is $CH_2$; $X_5$ is O.

In some embodiments, $X_1$ and $X_2$ are each C. In some embodiments, n is 1, and one or both of $X_1$ and $X_2$ are N.

In some embodiments, each $R_2$ is a substituent selected from Halo, $NO_2$, $CF_3$, $NR_3R_4$, $(C_1-C_6)$alkoxy, —C(O) $(C_1-C_6)$alkyl, $(C_3-C_8)$cycloalkyl, and —C(O)O($C_1-C_6$)alkyl. In some embodiments, $R_2$ is methyl, ethyl, methoxy, or isopropyl. In some embodiments, $R_2$ is Halo (e.g., F, Cl, Br, I). In some embodiments, m is 1. In exemplary embodiments, $R_2$ (or each $R_2$) is F.

In some embodiments, $R_3$ and $R_4$ together with the carbon to which they are attached form a $(C_3-C_8)$ cycloalkyl or $(C_3-C_8)$ heterocyclo. In some embodiments, substituents at $R_3$ and/or $R_4$ are sufficiently bulky to reduce interactions of the compound with DNA (e.g., reduce DNA intercalation). In some embodiments, $R_3$ and $R_4$ together with the carbon to which they are attached, form a 5-membered or 6-membered or 7-membered carbocyclic ring. In some embodiments, one of $R_3$ and $R_4$ is $(C_1-C_6)$ alkyl or $(C_2-C_6)$ alkenyl, and the other is H. In some embodiments, one of $R_3$ and $R_4$ are H. In some embodiments, $R_3$ is methyl, ethyl, methoxy, or isopropyl. In some embodiments, $R_4$ is methyl, ethyl, methoxy, or isopropyl.

In certain other embodiments, both of $R_3$ and $R_4$ can be H.

In some embodiments of Formula (II), each $R_1$ is OH, and n is 1 or 2; each $R_2$ is Halo (e.g., F or Cl), and m is 1 or 2; $R_3$ and $R_4$ together with the carbon to which they are attached form a 5-membered or 7-membered carbocyclic ring.

In one embodiment, the compound of Formula (II) has the structure:

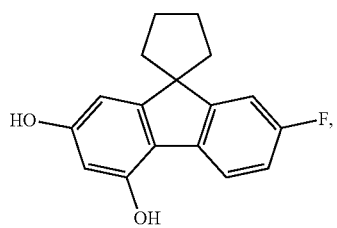 [SMILES: Oc1cc(O)c2c(c1)C1(CCCC1)c1cc(F)ccc1-2]

also referred to herein as ARTX-405A. Thus, in one embodiment, the compound of Formula (II) is 7'-fluorospiro[cyclopentane-1,9'-fluorene]-2',4'-diol.

In another embodiment, the compound of Formula (II) has the structure, referred to herein as ARTX-437:

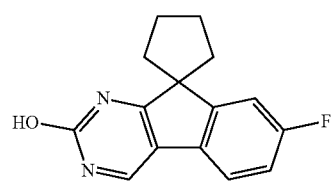 [SMILES: Oc1ncc2c(n1)C1(CCCC1)c1cc(F)ccc1-2]

In some embodiments, the compound of Formula (II) has the structure, referred to herein as ARTX-438:

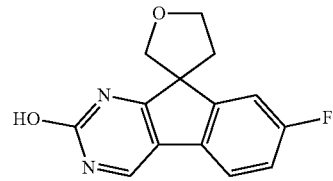 [SMILES: Oc1ncc2c(n1)C1(CCOC1)c1cc(F)ccc1-2]

In some embodiments, the compound of Formula (II) has the structure, referred to herein as ARTX-439:

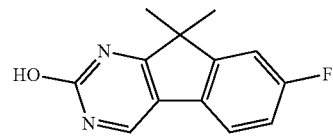 [SMILES: CC1(C)c2cc(F)ccc2-c2cnc(O)nc21]

In some embodiments, the compound of Formula (II) has the structure, referred to herein as ARTX-440:

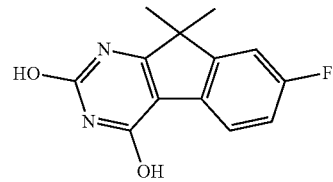 [SMILES: CC1(C)c2cc(F)ccc2-c2c(O)nc(O)nc21]

In various embodiments, the present disclosure provides a compound of Formula (III) or a pharmaceutically acceptable salt thereof.

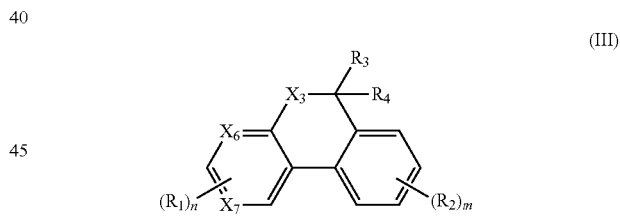

According to Formula (III):
each $R_1$ is independently selected from the group consisting of OH, $NO_2$, Halo, $CF_3$, $NR_3R_4$, $(C_1-C_6)$alkoxy, —C(O) $(C_1-C_6)$alkyl, and —C(O)O($C_1-C_6$)alkyl;
each $R_2$ is a substituent other than OH;
$R_3$ and $R_4$ are each independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo; with proviso that $R_3$ and $R_4$ cannot both be H;
$X_6$ and $X_7$ are each independently C or N;
$X_3$ is O or S;
m is an integer in the range of 1 to 4; and
n is an integer in the range of 1 to 4.
In some embodiments, $X_3$ is O.
In some embodiments, $R_1$ is OH.

In some embodiments, $X_6$ is N and $X_7$ is N. In some embodiments, $X_6$ is N and $X_7$ is C. In some embodiments, $X_6$ is C and $X_7$ is N. In some embodiments, $X_6$ is C and $X_7$ is C.

In some embodiments, each $R_2$ is selected from Halo, CN, $NO_2$, —C(O) ($C_1$-$C_6$)alkyl, ($C_1$-$C_6$)alkoxy, —C(O)O($C_1$-$C_6$)alkyl, aryl, heteroaryl, $NR_3R_4$, and $CF_3$. In some embodiments, $R_2$ is methyl, ethyl, methoxy, or isopropyl. In some embodiments, $R_2$ is Halo (e.g., independently selected from F, Cl, Br, or I). In some embodiments, each $R_2$ is Halo, and m is 1 or 2. For example, each $R_2$ may be F, and m is 1 or 2.

In some embodiments, $R_3$ and $R_4$ are each selected from alkyl, alkenyl, and cycloalkyl. For example, one of $R_3$ and $R_4$ may be isopropyl.

Alternatively, $R_3$ and $R_4$ together with the carbon to which they are attached, can form a ($C_3$-$C_8$) cycloalkyl or ($C_3$-$C_8$) heterocyclo.

In some embodiments, $X_3$ is O; each $R_1$ is independently selected from OH and halo; $X_6$ and $X_7$ are CH; n is 1; each $R_2$ is Halo, and m is 1, 2, or 3; and $R_3$ is alkyl or H, and $R_4$ is H.

In one embodiment, the compound of Formula (III) has the structure:

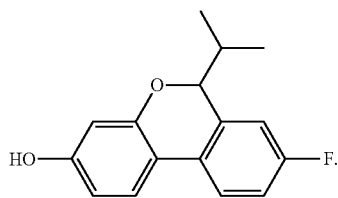

In one embodiment, the compound of Formula (III) has the structure:

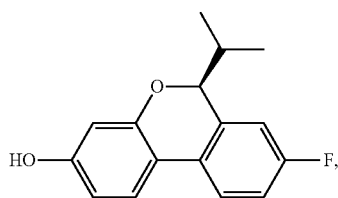 [SMILES: CC(C)[C@@H]1Oc2cc(O)ccc2-c2ccc(F)cc21]

referred to herein as ATRX-425P1.

In one embodiment, the compound of Formula (III) has the structure:

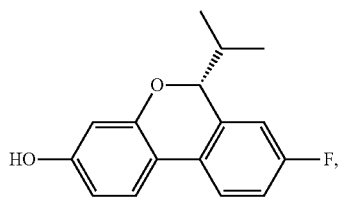

referred to herein as ARTX-425P2.

In one embodiment, the compound of Formula (III) has the structure:

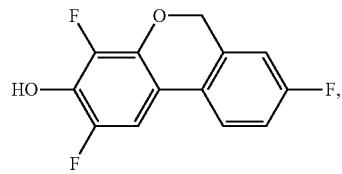 [SMILES: Oc1c(F)cc2c(c1F)OCc1cc(F)ccc1-2]

referred to herein as ARTX-408.

Figure 4:
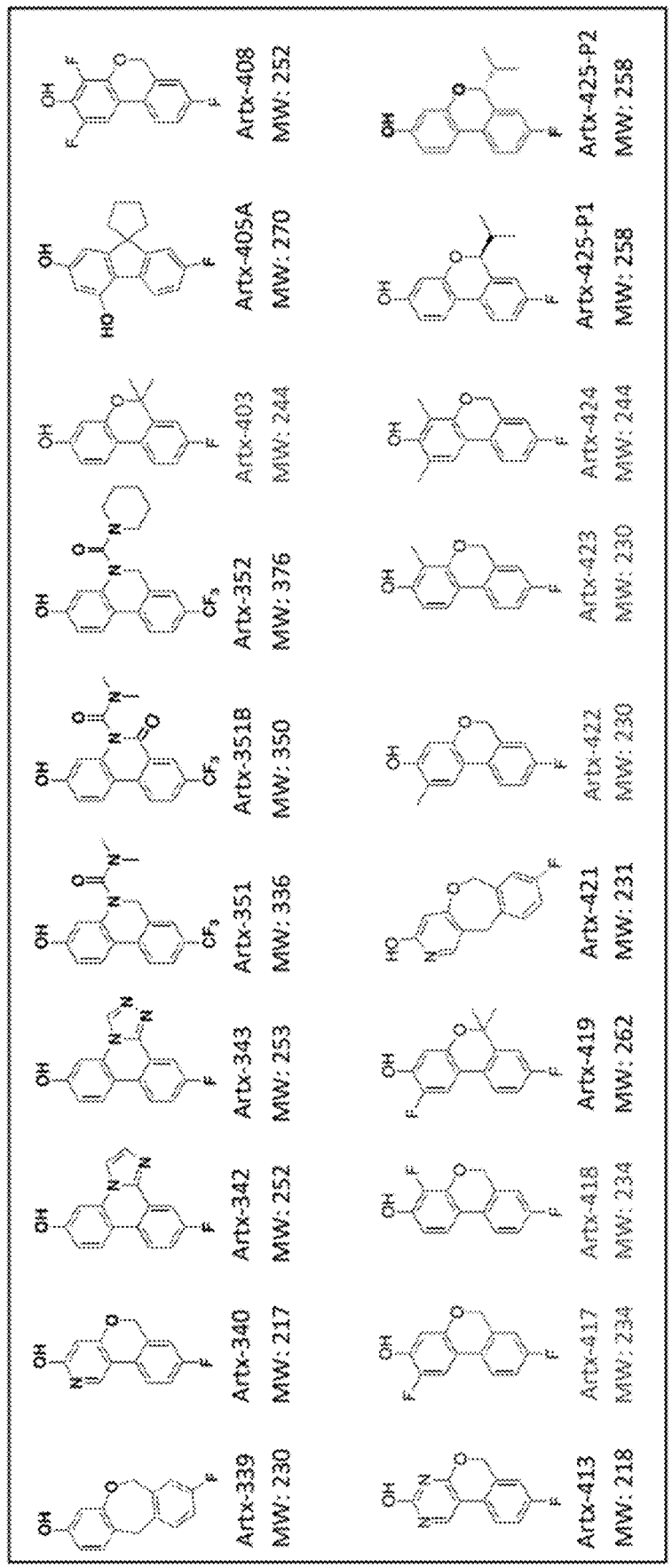
FIG. 4 shows the structure of exemplary compounds inspired from UAS03.

In some embodiments, the compound of the present disclosure has any one of the structures shown in FIG. 4.

In various embodiments, the compounds of Formula (I), (II) or (III) are agonists of the aryl hydrocarbon receptor (AhR) that activate the AhR signaling pathway. In various embodiments, the compounds of Formula (I), (II) or (III) are non-genotoxic, even with long term use. In various embodiments, the compounds of Formula (I), (II) or (III) do not show significant or substantial quinone formation. In various embodiments, the compounds of Formula (I), (II) or (III) are effective for enhancing the barrier integrity of epithelial and endothelial tissues, including in some embodiments the barrier function of the gastrointestinal tract.

In other aspects, the present disclosure provides a pharmaceutical composition comprising a compound of Formula (I), (II), or (III) or a pharmaceutically acceptable salt or solvate thereof, and a pharmaceutically acceptable excipient or carrier.

The pharmaceutical composition may comprise a pharmaceutically acceptable salt of the compound of Formula (I), (II), or (III). Any pharmaceutically acceptable salt can be employed, including those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002. Exemplary pharmaceutically acceptable salts can be selected from acetate, ascorbate, benzoate, benzenesulfonate, bisulfate, borate, butyrate, citrate, camphorate, camphor sulfonate, fumarate, hydrochloride, hydrobromide, hydroiodide, lactate, maleate, methanesulfonate, naphthalenesulfonate, nitrate, oxalate, phosphate, propionate, salicylate, succinate, sulfate, tartrate, thiocyanate, and toluenesulfonate salt.

In some embodiments, the composition is formulated for oral delivery to the gastrointestinal tract. Exemplary forms for oral delivery include tablets, capsules, solutions, and suspensions. In some embodiments, the composition is formulated for delivery to the small intestine and/or the large intestine. For example, the formulation can comprise a pH-dependent enteric coating (e.g., EUDRAGIT) that avoids release of the active agents at the low pH of the stomach, but which dissolves in the small and/or large intestine. Various enteric coatings can be selected to target portions of the small and/or large intestines, such as the duodenum, jejunum, ileum, or the colon. In some embodiments, the composition is formulated without an enteric coating.

In some embodiments, the composition is formulated for delivery to the lung. In such embodiments, the active agents enhance the epithelial and/or endothelial integrity in the lung. In some embodiments, the pharmaceutical composition is formulated as a solution or powder aerosol. In some embodiments, the composition is delivered locally to the lung by use of a nebulizer or inhaler.

In some embodiments, the composition is formulated for parenteral delivery, including for example by a route selected from intravenous, intraarterial, intramuscular, intradermal, intrathecal, and subcutaneous administration.

Other forms of administration, including for local or topical administration to target tissues, are contemplated by the disclosure. Examples of pharmaceutical compositions are described elsewhere herein.

In other aspects, the present disclosure provides methods for treating an epithelial or endothelial dysfunction disorder in a subject. The method comprises administering to a subject the compound of Formula (I), (II), or (III) or a pharmaceutically acceptable salt or solvate thereof, or the pharmaceutical composition thereof. In embodiments, the method induces the expression of tight junction proteins in a tissue. In exemplary embodiments, the subject has inflammation to be treated of one or more organs or tissues selected from intestine, liver, kidneys, pancreas, heart, lungs, skin, muscle, fat, brain, eyes, cars, mucosal membrane(s), bone, joints, marrow, and cartilage. Such inflammation can be mitigated through systemic or local treatment with the compounds and compositions, or by treatment of gut barrier function.

In various embodiments, the subject is an animal, such as a mammal, and may be a human subject. In some embodiments, the subject is a veterinary subject such as a cat, dog, horse, cow, sheep, birds etc.

In some embodiments, the subject has an inflammatory or metabolic disorder with epithelial or endothelial barrier dysfunction. In some embodiments, the inflammatory or metabolic disorder is an epithelial disorder of the gastrointestinal tract, such as inflammatory bowel disease or irritable bowel syndrome. Where the subject has inflammatory bowel disease, the subject may have ulcerative colitis or Crohn's disease. In other embodiments, the subject has a disorder selected from celiac disease, Whipple Disease, tropical sprue, colonic inflammation, and MIS-C/MIS/A. For example, the subject may exhibit symptoms of gastrointestinal permeability or inflammation, and the composition is administered to the small and/or large intestine (e.g., enterally).

In some embodiments, the subject has mucositis, such as oral mucositis or intestinal mucositis. In some embodiments, the subject has radiation-induced mucositis or intestinal permeability, or drug-induced mucositis or intestinal permeability. In some embodiments, the subject is undergoing radiation therapy or chemotherapy for cancer, resulting in mucositis, which can be prevented or ameliorated according to the present disclosure.

Other indications potentially associated with permeability of the gastrointestinal tract can include colon cancer, diverticular disease, colitis, immune checkpoint inhibitor-induced colitis, esophagitis (such as eosinophilic esophagitis), environmental enteropathy disorder (EED), gastrointestinal symptoms associated with HIV, pouchitis, gastric ulcer, ischemic intestinal condition, fatty liver disease and/or kidney disease, obesity, cardiovascular disease (CVD), and metabolic syndrome. In some embodiments, the subject has or is at risk of non-alcoholic steatohepatitis (NASH), alcoholic steatohepatitis (ASH), alcohol associated liver disease (AALD) (also called as alcoholic liver disease (ALD)), non-alcoholic fatty liver disease (NAFLD), or primary sclerosing cholangitis. In these or other embodiments, the subject has chronic kidney disease. In some embodiments, the subject has hepatitis or cirrhosis. In some embodiments, the subject has an inflammatory skin disease, such as atopic dermatitis, pemphigus, or psoriasis.

In some embodiments, the subject has organ fibrosis, and which is optionally fibrosis of the liver, kidney, heart, pancreas, or lung, which in some embodiments is associated with permeability of the gastrointestinal tract. In some embodiments, the subject has pancreatitis or idiopathic pulmonary fibrosis.

In some embodiments, the invention provides a method of enhancing airway barrier integrity in lungs. In these embodiments, the method comprises administering to a subject in need thereof an effective amount of a composition described herein. In various embodiments, the composition is administered systemically (e.g., enterally or parenterally) or locally to the lungs (e.g., by inhalation). In accordance with these embodiments, the active agent can reduce vascular permeability in the lungs, as well as the reduce permeability of the epithelial barrier. In some embodiments, the compound or composition reduces fibrosis. In some embodiments, the subject has pulmonary fibrosis (e.g., IPF), chronic obstructive pulmonary disease (COPD), acute lung injury, acute respiratory distress syndrome, or asthma.

In some embodiments, the subject has sepsis or septic shock, or is at risk of sepsis or septic shock. In these embodiments, the subject can exhibit gastrointestinal permeability and/or permeability of the vasculature.

In some embodiments, the subject has an immune or autoimmune condition, which may be associated with gastrointestinal permeability. For example, the subject may have a condition selected from food allergy, diabetes mellitus, scleroderma, celiac disease, dermatitis herpetiformis, atopic dermatitis, psoriasis, vasculitis, Sjogren's syndrome, rheumatoid arthritis, and multiple sclerosis. Active agents described herein can be administered to the gastrointestinal tract, or directly to affected tissues.

In some embodiments, the subject has a neuroinflammatory disorder, which may be associated with gastrointestinal inflammation in some embodiments. For example, the neuroinflammatory disorder may be Alzheimer's Disease, Parkinson's Disease, dementia, or multiple sclerosis. Other CNS disorders potentially treated according to this disclosure include panic disorder, social phobia, atypical depression, bipolar disorder, mixed anxiety disorder and depression, bulimia, post-traumatic stress disorder, borderline personality disorder, and migraine. Still other conditions include chronic fatigue syndrome, Long Covid (i.e., post COVID19 condition) and fibromyalgia.

In some embodiments, the neuroinflammatory disorder is Alzheimer's Disease or Parkinson's Disease, and the subject has early stage disease, where disease trajectory can be modified. In some embodiments, the neuroinflammatory disorder is a neurodegenerative disease, such as multiple sclerosis. In some embodiments, administration of compounds or compositions is direct to the CNS, such as by intrathecal administration or intranasal administration. In other embodiments, the administration is systemic administration (either by parenteral or enteral routes).

In some embodiments, the disorder is an epithelial or endothelial disorder of the lung, such as acute respiratory distress syndrome (ARDS) or acute lung injury (ALI).

In some embodiments, the disorder is a cardiovascular disease (CVD) where an increase in endothelial permeability is observed, including hypertension, coronary artery disease, atherosclerosis, heart failure, or myocardial infarction.

In some embodiments, the subject has a condition associated with endothelial barrier dysfunction or organ damage or inflammation. In some embodiments, the condition is vasculitis, sepsis, scleroderma, drug-induced internal bleeding, vascular permeability, capillary leak syndrome, diabetic retinopathy, diabetic macular edema, age-related macular degeneration (e.g., wet AMD), hepatitis, liver cirrhosis, primary sclerosing cholangitis, and pancreatitis. In some embodiments for treatment of conditions such as diabetic retinopathy, diabetic macular edema, age-related macular degeneration (e.g., wet AMD), composition can be applied locally as eye drops or by intraocular injection.

In various embodiments, the subject has a disease or condition selected from metabolic stress, cardiovascular disease, sarcopenia, muscle degenerative disease, Duchenne muscular dystrophy, drug-induced liver injury, chronic kidney disease, alpha-antitrypsin deficiency, ischemia/reperfusion injury, metabolic syndrome, type II diabetes mellitus, hyperlipidemia, osteoarthritis, neurodegenerative disease, amyotrophic lateral sclerosis (ALS), cognitive disorder, and mood disorder. The compound or composition, which may be a chronic dosing regimen, treats or ameliorates the disease or condition.

In some embodiments, the subject has cancer, and is optionally receiving chemotherapy, radiation therapy, or immune therapy (such as an immune checkpoint inhibitor therapy, e.g., PD-1 blockade therapy or anti-CTLA4 therapy). In some embodiments the cancer is a sarcoma, carcinoma, or solid tumor or cancer selected from germ line tumors, tumors of the central nervous system, breast cancer, prostate cancer, cervical cancer, uterine cancer, lung cancer, head and neck cancer, ovarian cancer, testicular cancer, thyroid cancer, astrocytoma, glioma, pancreatic cancer, stomach cancer, liver cancer, colon cancer, melanoma, renal cancer, bladder cancer, esophageal cancer, cancer of the larynx, cancer of the parotid, cancer of the biliary tract, rectal cancer, endometrial cancer, squamous cell carcinomas, adenocarcinomas, small cell carcinomas, neuroblastomas, mesotheliomas, adrenocortical carcinomas, epithelial carcinomas, desmoid tumors, desmoplastic small round cell tumors, endocrine tumors, Ewing sarcoma family tumors, germ cell tumors, hepatoblastomas, hepatocellular carcinomas, lymphomas, melanomas, non-rhabdomyosarcome soft tissue sarcomas, osteosarcomas, peripheral primitive neuroectodermal tumors, retinoblastomas, rhabdomyosarcomas, and Wilms tumors. In some embodiments, the cancer is colon cancer.

Exemplary chemotherapeutic agents include aminoglutethimide, amsacrine, anastrozole, asparaginase, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine, among others.

In various embodiments, the compositions are administered by parenteral administration for systemic administration or locally to a target tissue. The pharmaceutical compositions can be formulated for administration by any suitable route, including oral administration, transdermal administration, administration by inhalation, nasal administration, topical administration, intravaginal administration, ophthalmic administration, intra-aural administration, intracerebral administration, rectal administration, and parenteral administration. Some preferred routes include enteral, parenteral, inhalation, intranasal, rectal, and topical. In some embodiments, the compound of Formula (I), (II), or (III) is administered orally, and acts locally to improve intestinal barrier function, and is partially systemically absorbed for systemic benefits.

In some embodiments, the pharmaceutical composition is formulated for (i.e., suitable for) intravenous administration, for example, as an aqueous or non-aqueous solution or suspension. Systemic administration of the pharmaceutical compositions provides benefits for reducing systemic inflammation as well as improving integrity of endothelial tight junctions.

In some embodiments, the composition is an aerosol (including a powder or solution aerosol) or mist (e.g., which can be optionally delivered using a nebulizer) formulated for pulmonary administration.

In some embodiments, the composition is formulated for topical administration to the skin, eyes, ears, nose, throat, rectum, or mucus membrane.

In some embodiments, the composition is formulated for administration to the gastrointestinal tract. For example, in some embodiments, the composition is formulated for delivery of an effective amount of the compound of Formula (I), (II), or (III) to the mouth, esophagus, stomach, small intestine, large intestine, colon, and/or rectum. Compositions can be administered orally or locally to the rectum using suppositories or enema.

In some embodiments, the composition is formulated for systemic administration, including by enteral or parenteral routes.

In some embodiments, the composition is administered to the central nervous system of a subject. For example, the composition can be formulated for intranasal administration or intrathecal administration.

An exemplary dose (e.g., a unit dose) of the active agent (a compound of Formula (I), (II), or (III), such as ARTX-413, ARTX-405A, ARTX-425P1, or ARTX-339) is in the range of about 10 mg to about 1000 mg. For example, suitable doses may be in the range of about 25 mg to about 1000 mg, or from about 100 mg to about 1000 mg, or from about 100 mg to about 500 mg, or from about 100 mg to about 250 mg. In some embodiments, the dose (e.g. a unit dose) may be in the range of 200 mg to about 1000 mg, or from about 200 mg to about 750 mg, or from about 200 mg to about 500 mg. Such doses are administered from one to three times daily, for example. Exemplary daily doses may be in the range of 20 mg to about 3000 mg, such as from 100 mg to about 2000 mg, or from about 150 mg to about 2000 mg, or from about 150 mg to about 1000 mg, or from about 150 mg to about 750 mg. In some embodiments, the unit dose according to this paragraph is an oral dosage formulation for delivery to the gastrointestinal tract, or is an aerosol delivered by inhalation.

In some embodiments, the dosage is determined with regard to the size of the patient, that is, the active agent (a compound of Formula (I), (II), or (III), such as ARTX-413, ARTX-405A, ARTX-425P1, or ARTX-339) is administered at a dose in a range of about 1 mg/kg to about 25 mg/kg, or in the range of 1 mg/kg to about 10 mg/kg. In some embodiments, the composition is administered parenterally (e.g., by i.v.).

Exemplary pharmaceutically acceptable carriers include sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Compositions can also contain preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of an injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping drug in liposomes, lipid nanoparticles, or microemulsions which are compatible with body tissues. The injectable formulations can be sterilized, for example, by filtration through a bacterial-retaining filter or by incorporating sterilizing agents in the form of sterile solid compositions, which can be dissolved or dispersed in sterile water or other sterile injectable media just prior to use. Suitable inert carriers can include sugars such as lactose.

In some embodiments, the active agent is formulated as a tablet or capsule, or other solid dosage form for enteral administration. In some embodiments, the solid dosage form for enteral administration provides for local action in the gastrointestinal tract, as well as systemically by systemic absorption. In some embodiments, the pharmaceutical composition is formulated to deliver the active agent to one or more regions of the gastrointestinal tract exhibiting inflammatory symptoms or loss of tight junction integrity, such as, for example, the esophagus, stomach, duodenum, jejunum, ileum, colon transversum, colon descendens, colon ascendens, colon sigmoidenum, cecum, and rectum.

In some embodiments, the active agent may be administered to the colon of a patient, as an oral dosage, modified-release composition. For example, the formulation may employ a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with a hydroxypropyl methylcellulose barrier layer interposed in between. In another embodiment, colon delivery may be achieved by formulating the active agent with specific polymers that degrade in the colon such as, for example, pectin. The pectin may be further gelled or crosslinked with a cation such as a zinc cation. Additional colon specific formulations include, but are not limited to, pressure-controlled drug delivery systems (prepared with, for example, ethylcellulose) and osmotic controlled drug delivery systems (i.e., ORDS-CT).

In an embodiment, the composition may remain essentially intact, or may be essentially insoluble, in gastric fluid. In some embodiments, the stability of the coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

In some embodiments, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12.5, L 12.5 P, RL 30 D, RL PO, RL 100, RL 12.5, RS 30 D, RS PO, RS 100, RS 12.5, NE 30 D, NE 40 D, NM 30 D, S 100, S 12.5, and $12.5 P. In some embodiments, one or more of EUDRAGIT® FS 30D, L 30 D-55, L 100-55, L 100, L 12.5, L 12.5 P RL 30 D, RL PO, RL 100, RL 12.5, RS 30 D, RS PO, RS 100, RS 12.5, NE 30 D, NE 40 D, NM 30 D, S 100, S 12.5 and S 12.5 P is used. The enteric agent may be a combination of the foregoing solutions or dispersions.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, EUDRAGIT NE®, polyvinyl esters, polyvinyl acetals, polyacrylic acid esters, butadiene styrene copolymers, and the like.

In some embodiments, the active agent is formulated as a suppository for local action at the rectum or system action.

Exemplary ingredients to form the base of a suppository include, but are not limited to, cocoa butter or a similar substitute, polyethylene glycol, hydrogels, and glycerinated gelatin.

Topical compositions can be formulated as aqueous or non-aqueous solutions or suspension, creams, gels (e.g., hydrogels), ointments, foams, and the like. Exemplary excipients in topical compositions include, but are not limited to, emulsifiers and surfactants, including CREMOPHOR EL, lauramine oxide, myristyl dimethylamine oxide, polyoxyl 20 ceto stearylether, polyoxyl 40 hydrogenated castor oil, polyoxyl 23 lauryl ether, poloxamer 407, and carboxymethyl cellulose.

In the various embodiments, the compounds or compositions may be administered using a dosing schedule or regimen suitable for relief of disease symptoms and/or to reduce or mitigate disease activity or progression, or to enhance overall health. For example, compositions may be administered from one to three times daily or weekly. In some embodiments, the compositions are administered at least about daily or at least about weekly. Dosing regimens can be for at least about one week, at least about one month, or at least about six months, or can be continuous to reduce disease activity or to enhance overall health.

As used in this specification and the appended claims, the singular forms "a," "an" and "the" include plural referents unless the context clearly dictates otherwise. Thus, for example, reference to "a functional group," "an alkyl," or "a residue" includes two or more such functional groups, alkyls, or residues, and the like.

As used herein, the terms "optional" or "optionally" means that the subsequently described event or circumstance can or cannot occur, and that the description includes instances where said event or circumstance occurs and instances where it does not.

As used herein, the term "subject" or "patient" refers to a target of administration, and these terms are used interchangeably.

As used herein, the term "treatment" refers to the medical management of a patient with the intent to cure, ameliorate, or stabilize pathological condition or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause significant adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. In further various aspects, a preparation can be administered in a "prophylactically effective amount"; that is, an amount effective for prevention of a disease or condition.

The chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

The compounds of the present invention may contain asymmetric or chiral centers, and therefore, exist in different stereoisomeric forms. It is contemplated that all stereoisomeric forms of the compound(s) as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures thereof, are contemplated.

Mixtures of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the resulting diastereomers and then converting (e.g., hydrolyzing) the individual diastereomers to the corresponding pure enantiomers.

The term "H" denotes a single hydrogen atom, and is not a substituent.

Where the term "alkyl" is used, either alone or within other terms such as "haloalkyl" or "alkylamino", embraces linear or branched hydrocarbon radicals. Exemplary alkyls have from one to about thirty carbon atoms (or in some embodiments one to eight carbon atoms, or from one to four carbon atoms). Examples of alkyls include methyl, ethyl, n-propyl, isopropyl, n-butyl, isobutyl, sec-butyl, tert-butyl, pentyl, isoamyl, hexyl and the like. The term "alkylenyl" or "alkylene" embraces bridging divalent alkyl radicals such as methylenyl or ethylenyl.

The term "alkenyl" embraces linear or branched hydrocarbon radicals having at least one carbon-carbon double bond. Exemplary alkenyl groups have from two to about thirty carbon atoms (or in some embodiments one to eight carbon atoms, or from one to four carbon atoms). Examples of alkenyl radicals include ethenyl, propenyl, allyl, propenyl, butenyl and 4-methylbutenyl. The term "alkenyl" embraces radicals having "cis" and "trans" orientations, or alternatively, "E" and "Z" orientations.

The term "alkynyl" denotes linear or branched radicals having at least one carbon-carbon triple bond. Exemplary alkynyl groups have two to about thirty carbon atoms (or in some embodiments one to eight carbon atoms, or from one to four carbon atoms). Examples of such radicals include propargyl, and butynyl, and the like.

Alkyl, alkylenyl, alkenyl, and alkynyl substituents (including as described for compounds of Formula (I), (II), or (III) may be optionally substituted with one or more functional groups such as halo, hydroxy, nitro, amino, cyano, haloalkyl, aryl, heteroaryl, and heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl" embraces linear or branched alkyl radicals, e.g., having one to about thirty carbon atoms (or from one to eight or from one to four carbon atoms) any one of which may be substituted with one or more hydroxyl radicals. Examples of such radicals include hydroxymethyl, hydroxyethyl, hydroxypropyl, hydroxybutyl and hydroxyhexyl.

The term "alkoxy" embraces linear or branched oxy-containing radicals each having alkyl portions, e.g., of one to about thirty carbon atoms (or from one to eight or from one to four carbon atoms). Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or more rings, wherein such rings may be attached together in a fused manner. The term "aryl" embraces aromatic radicals such as phenyl, naphthyl, indenyl, tetrahydronaphthyl, and indanyl. An "aryl" group may have one or more substituents such as lower alkyl, hydroxyl, halo, haloalkyl, nitro, cyano, alkoxy, and lower alkylamino, and the like.

The term "heterocyclyl" (or "heterocyclo") embraces saturated, partially saturated and unsaturated heteroatom-containing ring radicals, where the heteroatoms may be selected from nitrogen, sulfur and oxygen. It does not include rings containing —O—O—, —O—S— or —S—S— portions. The "heterocyclyl" group may have one to four substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heteroaryl radicals include quinolyl, isoquinolyl, imidazolyl, pyridyl, thienyl, thiazolyl, oxazolyl, furyl and pyrazinyl. Other heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, and benzothienyl, and the like.

Particular examples of partially saturated and saturated heterocyclyl include pyrrolidinyl, imidazolidinyl, piperidinyl, pyrrolinyl, pyrazolidinyl, piperazinyl, tetrahydropyranyl, thiazolidinyl, dihydrothienyl, 2,3-dihydro-morpholinyl, benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-12'-benzo[d]isothiazol-6-yl, dihydropyranyl, dihydrofuryl and dihydrothiazolyl, and the like.

The term "heterocyclo" thus encompasses the following ring systems:

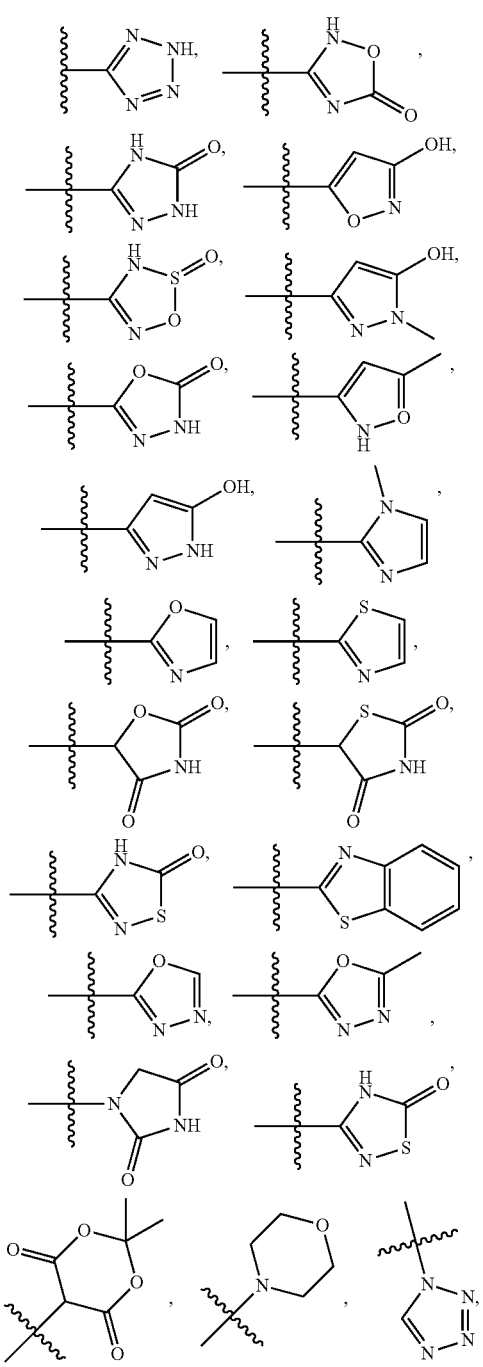

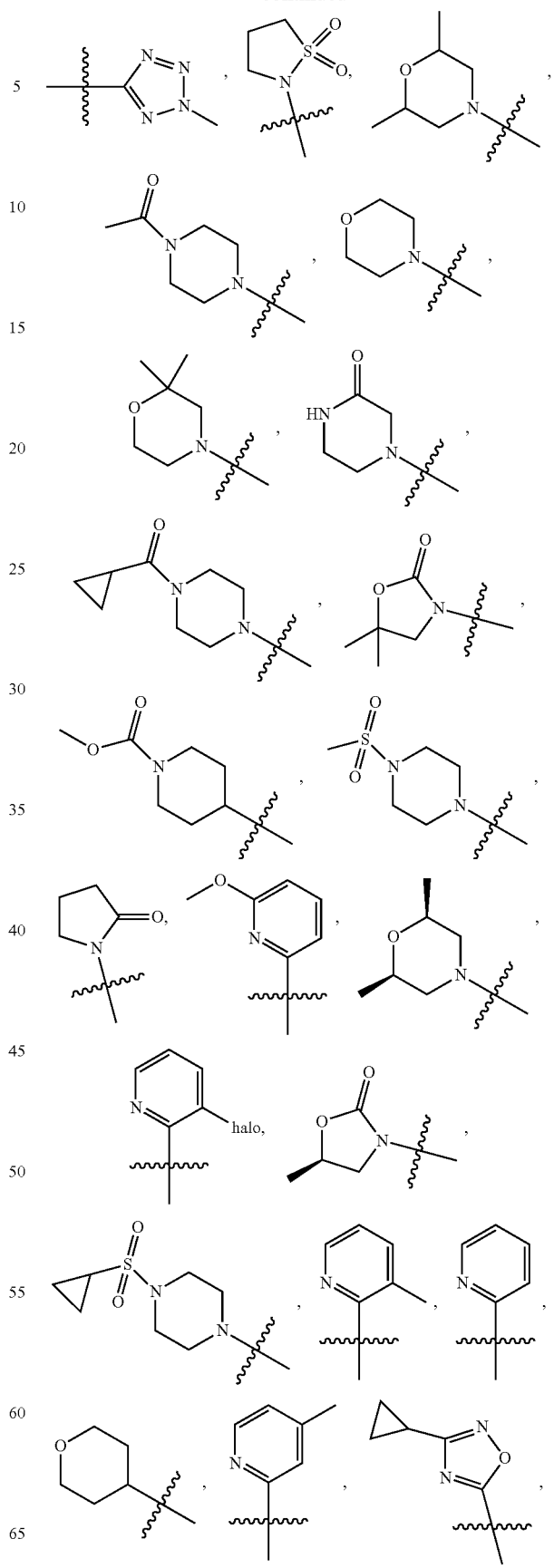

-continued

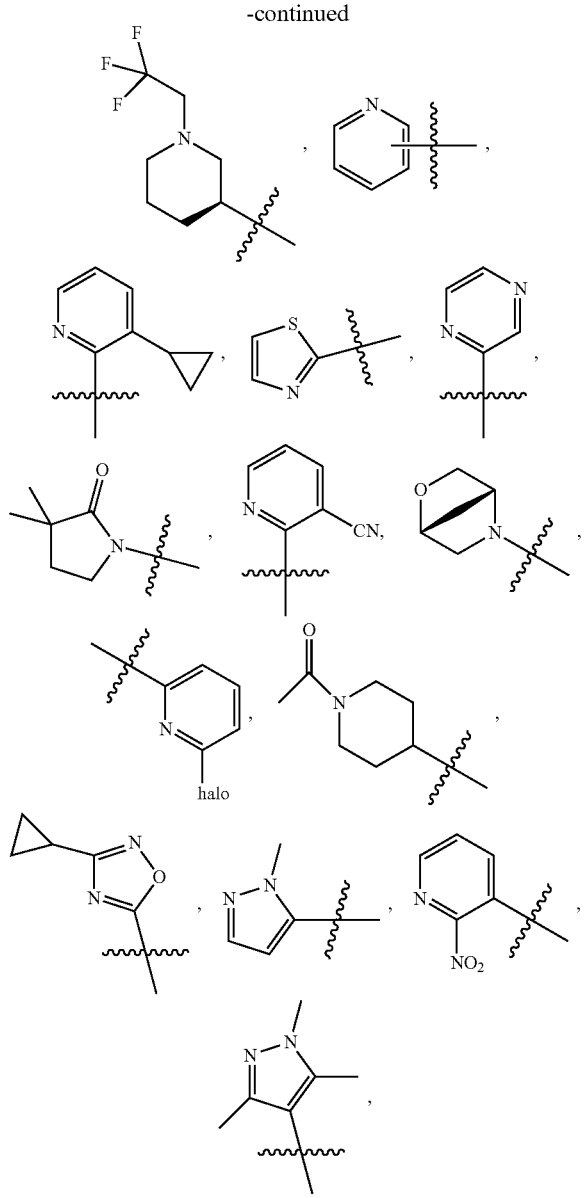

and the like.

The terms "carboxy" or "carboxyl," whether used alone or with other terms, such as "carboxyalkyl," denotes —CO$_2$H.

The term "carbonyl," whether used alone or with other terms, such as "aminocarbonyl," denotes —(C=O)—.

The term "cycloalkyl" includes saturated carbocyclic groups. Example of such radicals include, cyclopentyl, cyclopropyl, and cyclohexyl.

The term "cycloalkenyl" includes carbocyclic groups having one or more carbon-carbon double bonds including "cycloalkyldienyl" compounds.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

The symbol "-" represents a covalent bond and can also be used in a radical group to indicate the point of attachment to another group. In chemical structures, the symbol is commonly used to represent a methyl group in a molecule.

The term "excipient" means any pharmaceutically acceptable additive, carrier, diluent, adjuvant, or other ingredient, other than the active pharmaceutical ingredient (API), which is typically included for formulation and/or administration to a patient.

The term "therapeutically effective amount" means an amount of a compound that ameliorates, attenuates or eliminates one or more symptom of a particular disease or condition, or prevents or delays the onset of one of more symptoms of a particular disease or condition.

The term "pharmaceutically acceptable" means that the referenced substance, such as a compound or composition described herein, or a salt thereof, or a formulation containing a compound described herein, or a particular excipient, are suitable for administration to a patient.

As used herein, the term "about" means±10% of an associated numerical value.

All patents, published patent applications, and other publications recited herein are hereby incorporated by reference.

Those of ordinary skill in the art may make modifications and variations in the embodiments described herein without departing from the spirit or scope of the present disclosure.

Unless otherwise defined, all technical and scientific terms used herein have the same meaning as commonly understood by one of ordinary skill in the art to which this invention belongs.

Other aspects and embodiments of the invention will be apparent from the following Examples.

EXAMPLES

The present teachings, having been generally described, will be more readily understood by reference to the following examples.

Example 1: UroA and UAS03 Enhance Intestinal Epithelial Barrier Function Via the Aryl Hydrocarbon (AhR) and Nuclear Factor Erythroid 2-Related Factor 2 (Nrf2) Signaling Pathways The UrolithinA (UroA) lactone ring makes it acid labile and sensitive to hydrolytic enzymes (see FIG. 1). The UroA cyclic ester was converted to an ether, making the compound designated as UAS03, which is stable for at least 12 hours at pH 2.0 in the presence of gastric enzymes (whereas UroA is rapidly hydrolyzed under the same conditions)[44]. Similar to UroA[36-43], UAS03 also markedly decreased levels of lipopolysaccharide (LPS)-induced TNF-α, IL-6, CXCL-1, and IL-1β in bone marrow derived macrophages as well as in an LPS-elicited mouse peritonitis model[44]. RNA-seq and qRT-PCR analysis in HT-29 and Caco-2 intestinal epithelial cell lines showed that UAS03 upregulates the expression of the tight junction proteins (TJPs) claudin 4, ZO-1, and occludin 1[44]. UAS03 reversed LPS-induced permeability in Caco2 or HT-29[44] cell monolayers in transwell assays. UAS03 also activated the expression of cytochrome P450 1A1 (Cyp1A1) and heme oxygenase 1 (HMOX1 or HO1) genes[44], which function downstream of AhR[62] and Nrf2[63], respectively. Importantly, the barrier protective activities of UAS03 is dependent on expression of the AhR and Nrf2 pathways[44], consistent with published data showing that UroA is an AhR ligand that activates the AhR signaling pathway[64]. Experiments with AhR and Nrf2 knockout cell lines and Nrf2$^{-/-}$ or AhR$^{-/-}$ mice support the model that UroA and UAS03 activate the AhR pathway, which leads to the activation of the Nrf2 pathway and the expression of TJPs[44].

AhR is a ligand dependent transcription factor that binds to a range of endogenous and exogenous aromatic molecules including several compounds derived from the diet and gut microbiota[65-67]. Accumulating evidence indicates that AhR modulates intestinal epithelial barrier function[50-52] and that lack of AhR or its ligands compromises gut barrier integrity[53,54,68,69]. The discovery of endogenous AhR ligands suggests an important role for AhR in normal homeostatic processes unrelated to its role in the detection of xenobiotic toxins[65-67,46]. Finally, natural microbial tryptophan metabolites that are AhR ligands ameliorate intestinal barrier dysfunction in animal models of ulcerative colitis[51], suggesting that AhR-based therapies may restore barrier function in IBD.

Example 2: UAS03 in the Murine TNBS and DSS Models of Ulcerative Colitis

Intra-rectal administration of 2,4,6-Trinitrobenzenesulfonic acid (TNBS) induces CD4$^+$-dependent colitis in mice resulting in increased intestinal permeability, shortening of colons, and increased inflammation[70]. When administered orally QD or BID for three days following TNBS treatment, UAS03 at 20 mg/kg dramatically reversed the UC symptoms (FIGS. 2A-D)[44]. UAS03 also blocked the development of TNBS-elicited symptoms when mice were pre-treated QD for 7 days with UAS03 at 20 mg/kg. The symptoms that were reversed included body weight loss, colon weight/length ratio (FIG. 2A), increased gut permeability (FIG. 2B), and enhanced levels of inflammatory cytokines (FIG. 2C)[44]. UAS03 treatment induced the expression of tight junction protein, claudin 4 (cldn4). Importantly, UAS03 also reversed a dramatic decrease in claudin 4 (Cldn4) protein levels in the TNBS-treated mice (FIG. 2D). The beneficial effects of UAS03 in TNBS-treated mice were not observed in either AhR$^{-/-}$ or Nrf2$^{-/-}$ mutant mice[44]. UAS03 was about 10-fold more potent than UroA in the TNBS model, presumably due to its enhanced stability[44]. UAS03 was also efficacious in both acute and chronic dextran sodium sulfate (DSS)-induced[71,72] colitis models[44]. In the chronic model, mice were given 4 cycles of 2% DSS in drinking water for 7 days with an interval of 14 days in each cycle on regular water (total 90 day experiment). These mice received UAS03 QD at 20 mg/kg on days 4 and 6 of the DSS treatment cycle and on day 7 of the water cycle. Treatment with UAS03 protected against DSS-induced chronic colitis. UAS03 data from the TNBS and DSS experiments published are summarized in Table 1[44].

TABLE 1

UAS03 attenuates symptoms in murine models of Ulcerative Colitis (UC) based on colon length, intestinal permeability, histological examination, and diarrhea score.

| Method of Induction of UC Symptoms | Acute/Chronic Disease | UAS03 Dose | Prophylactic/ Therapeutic |
|---|---|---|---|
| 2.5 mg/mouse TNBS intrarectally | Acute | 4 mg/kg | Therapeutic |
| 2.5 mg/mouse TNBS intrarectally | Acute | 20 mg/kg | Prophylactic |
| 3% DSS in drinking water | Acute | 4 mg/kg | Therapeutic |
| 2% DSS in drinking water | Chronic | 20 mg/kg | Therapeutic |

Figure 3A:
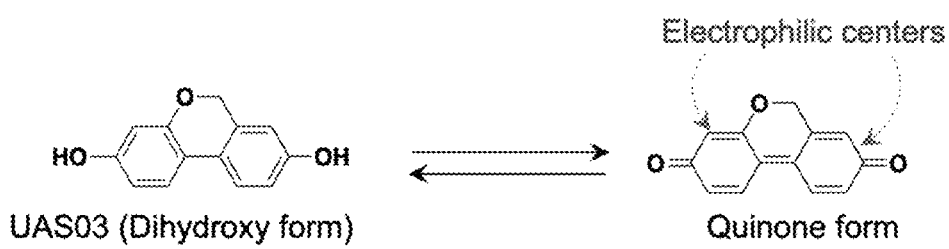
FIGS. 3A-B illustrates the potential liability of UAS03 to form reactive quinones.
Figure 3B:
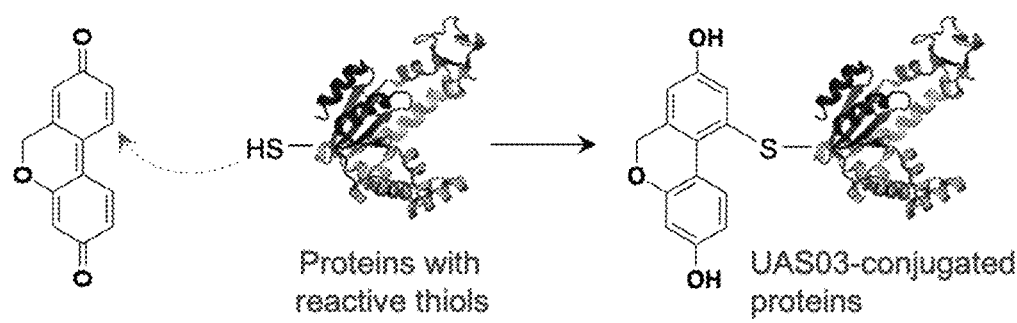

Despite its bioactivity, UAS03 is not believed to be a viable candidate for development as a therapeutic. UAS03 (as well as UroA) are predicted to form quinones, highly reactive molecules that are associated with "false-positive" hits in chemical library screens and long-term toxicity due to their reactivity (See FIG. 3B). Another concern with the UAS03 and UroA scaffolds is that they are planar molecules and can potentially intercalate into the DNA helix and form reactive metabolites that covalently bind to DNA bases resulting in genotoxicity. Although UroA is not known to be genotoxic, some UroA analogues with the same planar structure test positive in Ames test, suggesting that these structures could be genotoxic (especially if stabilized with an ether bond). It is therefore believed that careful compound design is necessary to avoid planarity and/or reactive hydroxyl groups, for example, that can be metabolized to highly reactive species.

Example 3: Compound Screening Process

Compounds whose structures were inspired by UroA and UAS03 but which cannot form quinones and/or which are unlikely to be non-genotoxic because they are non-planar and/or lack reactive hydroxyl moieties were designed (FIG. 4) and synthesized according to the general schemes shown in Example 9.

The following steps illustrates the procedure used to screen UroA- and UAS03-inspired compounds.

Step 1: Compounds were tested at 25 µM in the EpiIntestinal tissue model using TEER and/or FITC-Dextran assays to identify structures with comparable activity as UAS03 and UroA in restoration of LPS-disrupted barrier function. This "EpiIntestinal" transwell model incorporates enterocytes, Paneth cells, M cells, tuft cells, intestinal stem cells, and an underlying lamina propria into a differentiated, polarized epithelium[73]. The model exhibits functional tight junctions and brush borders at the apical tissue surface, which mimics many aspects of normal intestinal function including gut barrier function and inflammatory responses[73]. The rationale for first testing compounds in the EpiIntestinal permeability model is that the model, which is relatively high throughput in 96 well plates, tests directly for efficacy in the enhancement of barrier function.

Step 2: Selected compounds from step 1 were tested at a range of concentrations for activation of Cyp1A1 mRNA levels using qRT-PCR, for activation of Cyp1A1 enzymatic activity (ethoxyresorufin-O-deethylase (EROD) assay), or activation of an AhR-reporter gene driven by a so-called dioxin-response element (DRE) using commercially available kits. Activation of Cyp1A1 mRNA levels, activation of Cyp1A1 enzymatic activity, or activation of an AhR reporter gene construct driven by a DRE is generally considered to be indicative of a compound's ability to function as an AhR ligand. When activated by a ligand, cytosolic AhR translocates to the nucleus and dimerizes with the AhR nuclear translocator protein ARNT. The AhR/ARNT complex then binds to DREs to activate gene transcription.

Step 3: A limited number of compounds were tested from step 2 in the murine DSS model of ulcerative colitis to identify compounds with comparable efficacy as UAS03/UroA at 10 and/or 20 mg/kg.

Step 4: Toxicity studies, including hERG and Ames tests, are conducted on compounds.

Example 4: Potency and Efficacy of ARTX-86

ARTX-86 has the following chemical structure:

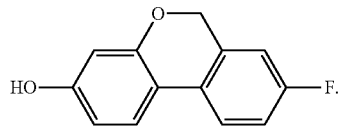

Following the procedure described in Example 3, it was found that ARTX-86, a compound designed not to be able to form quinones, was comparable in its potency and efficacy as UAS03 in enhancing intestinal epithelial barrier function in the 3D EpiIntestinal tissue model. ARTX-86 was also equally efficacious as UAS03 in the DSS and TNBS mouse models of UC. ARTX-86 was also comparably active as UroA and UAS03 in activating the expression of Cyp1A1. Moreover, ARTX-86 did not exhibit any observable acute toxicity in rats (MTD>2000 mg/kg; NOAEL=1000 mg/kg/day), was not cardiotoxic in an hERG assay up to 60 times the efficacious dose, and exhibited favorable PK properties in preliminary studies in rats ($C_{max}$=92±15 ng/mL when dosed at 20 mg/kg; $T_{1/2}$=2.22±0.5 hr). However, when ARTX-86 was subjected to an Ames Test, one of the *Salmonella* strains tested positive in the presence but not the absence of liver S9 enzymes, suggesting that ARTX-86 can be metabolized into a potentially genotoxic compound. This was unexpected because UroA has been extensively tested for genotoxicity and no indications of genotoxicity have been reported. However, potential genotoxicity of ARTX-86 is consistent with its planar structure, which may allow ARTX-86 to intercalate into the DNA double helix. It's possible that reactive metabolites of ARTX-86 are being formed by the S9 fraction and the ability of ARTX-86 to intercalate into the DNA helix delivers the radicals or other toxic metabolites directly to the DNA.

Figure 5:
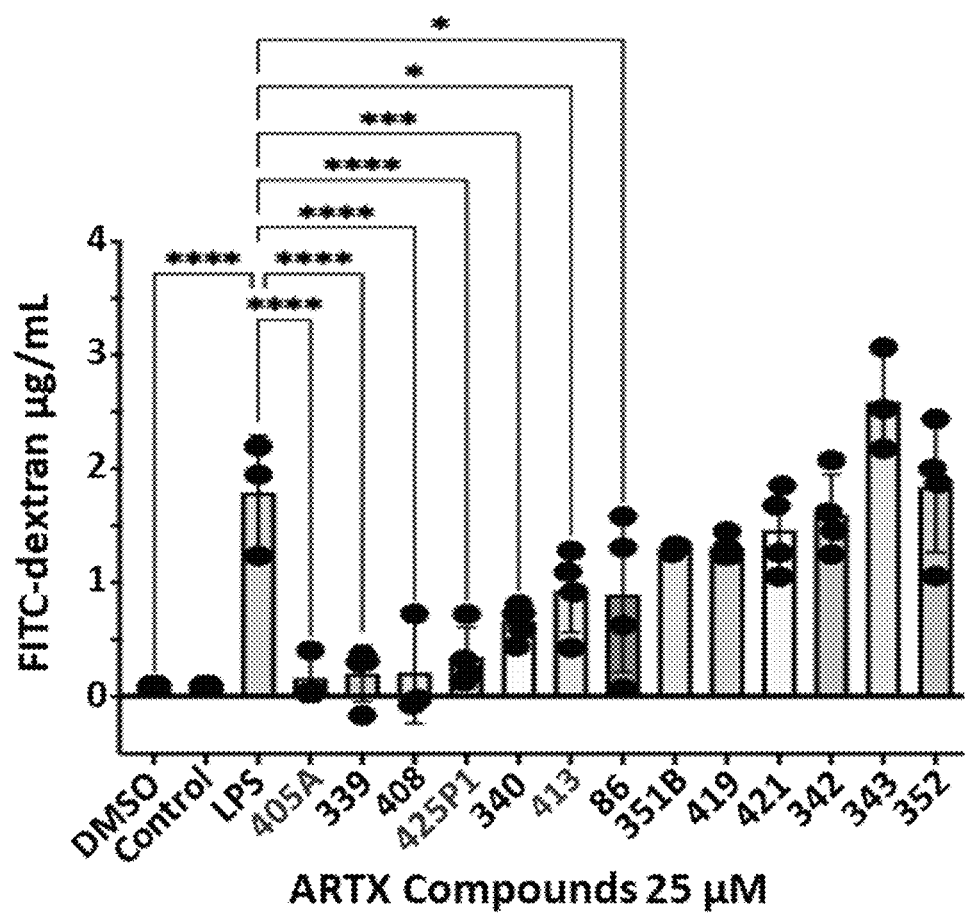
FIG. 5 illustrates the results of compounds tested in the human EpiIntestinal 3D in vitro tissue model. This model system incorporates enterocytes, paneth cell, M cells, tuft cells and intestinal stem cells into a highly differentiated, polarized epithelium. The EpiIntestinal tissue model recapitulates many aspects of normal intestinal function including barrier, metabolism, inflammatory and toxicity responses, similar to native human intestinal tissue. Important features of EpiIntestinal tissue include the presence of functional tight junctions and brush borders at the apical tissue surface (EpiIntestinal 3D in vitro Microtissues, purchased from MatTek Life Sciences). EpiIntestinal 3D tissues in 96-trans well plates were treated with 500 ng/ml LPS for 24 hours to disrupt barrier function and then treated with the test compounds at 25 µM for an additional 24 hours in the presence of 250 ng/mL LPS. FITC-dextran permeability assays were carried out by adding FITC-dextran (1 mg/mL) in the upper chamber and determining leakiness of FITC-dextran into the lower chamber after 2 h for each of the treatments. ** indicates p<0.0001; * indicates p<0.001; * indicates p≤0.05.

Example 5: ARTX-405A, ARTX-413, and ARTX-425P1 are Efficacious in Reducing LPS-Induced Intestinal Permeability in the EpiIntestinal Tissue Model After the finding that ARTX-86 was positive in the Ames test for genotoxicity (Example 4), only compounds designed to be non-genotoxic (e.g., because they are non-planar and/or because they do not contain reactive hydroxyl moieties) were subjected to the screening steps described in Example 3. This led to the discovery that several such compounds were as efficacious or more efficacious than ARTX-86 in reducing intestinal permeability in the EpiIntestinal tissue model including ARTX-405A, ARTX-413, and ARTX-425P1 as shown in FIG. 5.

Example 6: ARTX-339, ARTX-405A, ARTX-413, and ARTX-425P1 are Efficacious in the Mouse DSS UC Model A murine dextran sodium sulfate (DSS)-elicited model of ulcerative colitis was utilized to measure the efficacy of compounds in vivo. Oral administration of DSS in drinking water, a chemical colitogen with anticoagulant properties, leads to disruption of gut epithelium causing enhanced gut permeability, inflammation, and severe damage of gut barrier function[71,72]. The rationale for using the murine DSS[71,72] model of UC is that it is a well-established gut epithelial barrier disrupting model that can be used to model both acute and chronic UC[70,71]. An acute DSS-elicited model was used to test the effects of ARTX-339, ARTX-405A, ARTX-413, and ARTX-425P1 that reduced LPS-induced permeability in the human in vitro EpiIntestinal organoid tissue model. Most of these compounds, in addition to not being able to form quinones, were designed to be non-genotoxic because they are non-planar and/or do not contain reactive hydroxyl moieties.

As illustrated in FIG. 6A, C57BL/6 mice (7-8-week old mice) were supplied with 2.5% DSS in their drinking water for 7 days. Starting on day 4 post DSS treatment, mice were dosed once every other day with 100 μL vehicle (0.25% sodium carboxymethylcellulose used in the formulation of ARTX compounds), or 100 μL ARTX-339, ARTX-405A, ARTX-413, or ARTX-425P1 at 20 mg/kg body weight by oral gavage on days 4, 6, 8, and 10. Mice were euthanized on day 12. FITC dextran was administered to the mice via oral gavage 4 hours prior to euthanization. Following euthanization, colons were dissected, and their lengths were measured.

In FIGS. 6A-F, a total of 5 mice were used in each experimental group. Each of ARTX-339, ARTX-405A, ARTX-413, and ARTX-425P1 exhibited efficacy in the murine DSS model of colitis. FIGS. 6A-F show that ARTX-405A and ARTX-413 are highly effective in this model as measured by their ability to increase colon lengths (FIG. 6B and FIG. 6C), decrease intestinal permeability (FIG. 6D), protect from DSS-elicited reduced body weight (FIG. 6E), and decrease the disease activity index (DAI) (FIG. 6F). In the case of ARTX-339 and ARTX-425P1, although a statistically significant increase in colon length was not observed, each of ARTX-339 and ARTX-425P1 exhibited highly statistically significant data with respect to reducing intestinal permeability (FIG. 6D) as well as reducing body weight loss (FIG. 6E) and reducing the DAI (FIG. 6F). ** indicates $p<0.0001$; * indicates $p<0.001$; ** indicates=$p<0.01$.

Example 7. ARTX-413 Activates the AhR Signaling Pathway

FIGS. 7A-B illustrate the ability of ARTX-413 to activate the AhR signaling pathway. In these experiments, human hepatic cells (FIG. 7A) or human intestinal epithelial cells (FIG. 7B) containing a luciferase AhR-reporter gene construct driven by a so-called dioxin-response element (DRE) were treated with various concentrations of ARTX-413 or with various concentrations of the well-studied AhR ligand β-naphthoflavone (BNF) using commercially available kits. Activation of Cyp1A1 mRNA levels, activation of Cyp1A1 enzymatic activity, or activation of an AhR reporter gene construct driven by a DRE is generally considered to be indicative of a compound's ability to function as an AhR ligand.

Example 8. Toxicity Testing of ARTX-413

Figure 8:
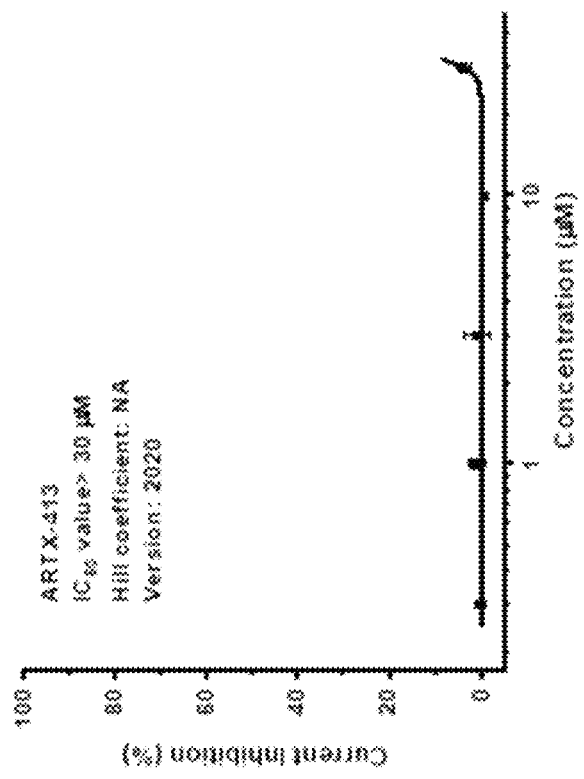
FIG. 8 illustrates the hERG inhibition of ARTX-413, indicating that ARTX-413 has very low risk in cardiotoxicity.

An Ames test showed that ARTX-413 is non-genotoxic, even at concentrations as high as 1.0 mg/mL. FIG. 8 shows results of ARTX-413 in the hERG assay, suggesting that ARTX-413 has low risk of cardiotoxicity. Further, in vitro safety pharmacology assays did not identify any significant off-target effects.

Example 9: Synthetic Schemes

Figure 9:
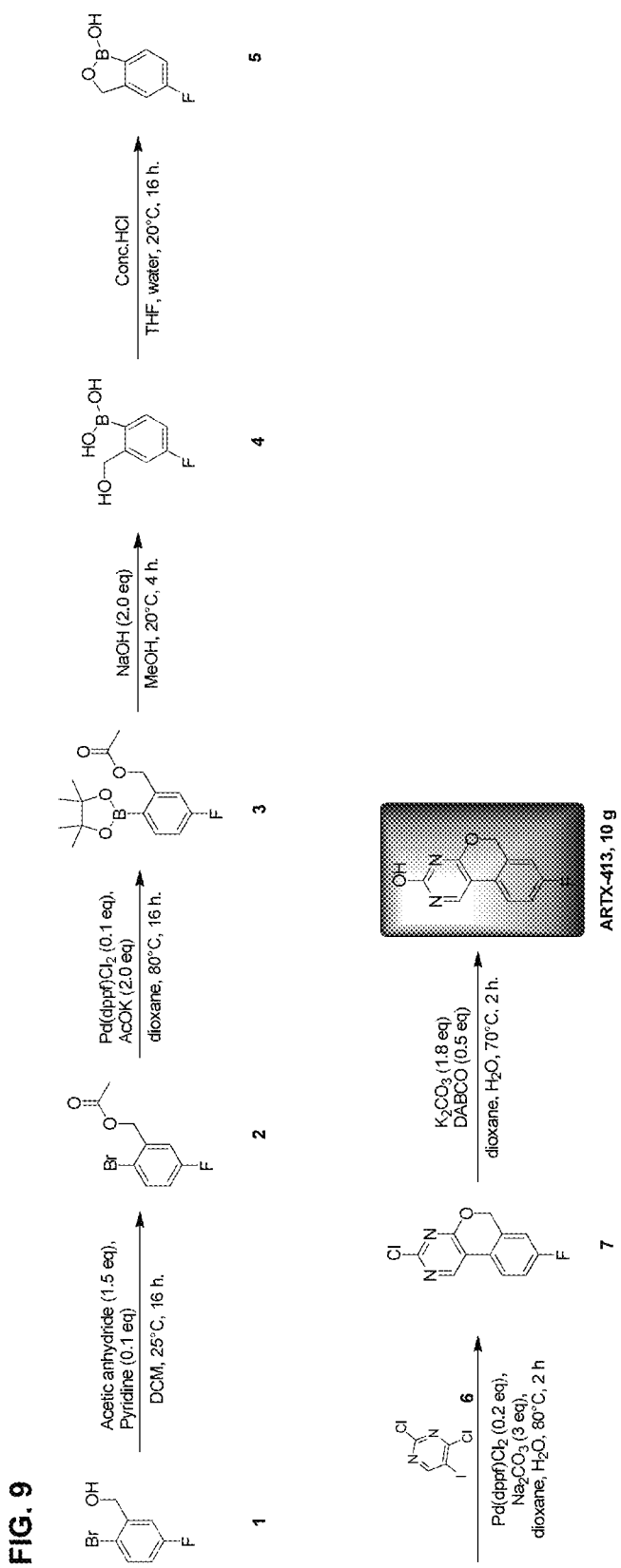
FIG. 9 shows a synthetic scheme for the synthesis of ARTX-413.

A synthetic scheme for the synthesis of ARTX-413 is shown in FIG. 9.

Preparation of 2-bromo-5-fluorobenzyl acetate (Compound 2 in FIG. 9)

To a solution of (2-bromo-5-fluoro-phenyl) methanol (100 g, 487.75 mmol, 1.00 eq) and $Ac_2O$ (74.69 g, 731.62 mmol, 68.52 mL, 1.50 eq) in DCM (500 mL) was added Pyridine (3.86 g, 48.77 mmol, 3.94 mL, 0.1 eq) dropwise at 25° C. and the resulting mixture was stirred at 25° C. for 16 h. The mixture was quenched with saturated sodium bicarbonate aqueous solution (200 mL) and stirred at 20° ° C. for 1 h, the organic phase was washed with saturated sodium bicarbonate aqueous solution (200 mL*2), 1 N HCl aqueous solution (200 mL), water (500 mL) and brine (500 mL), then dried over anhydrous sodium sulfate, filtered and concentrated in vacuum to give a residue. The crude was used directly without further purification. 2-bromo-5-fluorobenzyl acetate (105 g, 425.00 mmol, 87.13% yield) was obtained as a colorless crystalline solid.

Preparation of 5-fluoro-2-(4,4,5,5-tetramethyl-1,3,2-dioxaborolan-2-yl)benzyl acetate (Compound 3 in FIG. 9)

To a solution of 2-bromo-5-fluorobenzyl acetate (50 g, 202.38 mmol, 1.00 eq) in dioxane (600 mL) were added AcOK (56.00 g, 570.60 mmol, 2.82 eq) and BIS(PINACOLATO)DIBORON (56.00 g, 220.53 mmol, 1.09 eq). The resulting mixture was degassed and purged with nitrogen for 3 times, then $Pd(dppf)Cl_2$ (2.50 g, 3.42 mmol, 1.69e-2 eq) was added, the mixture was heated to 80° C. and stirred at 80° ° C. for 16 h. The mixture was cooled and quenched with water (500 mL) and extracted with ethyl acetate (500 mL*3). The collected layers were washed with water (1000 mL) and brine (1000 mL), dried over anhydrous sodium sulfate, filtered and concentrated in vacuum to give a residue. The crude was used directly without further purification. 5-fluoro-2-(4,4,5,5-tetramethyl-1,3,2-dioxaborolan-2-yl)benzyl acetate (65 g, 194.47 mmol, 96.09% yield, 88% purity) was obtained as a yellow oil.

Preparation of (4-fluoro-2-(hydroxymethyl)phenyl)boronic acid (Compound 4 in FIG. 9)

To a solution of 5-fluoro-2-(4,4,5,5-tetramethyl-1,3,2-dioxaborolan-2-yl)benzyl acetate (140 g, 475.99 mmol, 1 eq) in MeOH (40 mL) was added NaOH (38.08 g, 951.97 mmol, 2 eq), and the mixture was stirred at 20° C. for 4 h. The mixture was concentrated in vacuum to give a residue. The crude was used directly without further purification. (4-fluoro-2-(hydroxymethyl)phenyl)boronic acid (81 g, crude) was obtained as a white solid.

Preparation of 5-fluorobenzo[c][1,2]oxaborol-1(3H)-ol (Compound 5 in FIG. 9)

To a solution of (4-fluoro-2-(hydroxymethyl)phenyl)boronic acid (81 g, 476.62 mmol, 1 eq) in THF (480 mL) and Water (240 mL) was added HCl (12 M, 210.21 mL, 5.29 eq) dropwise at 25° C. over 5 min, and the resulting mixture was stirred at 25° C. for 16 h. The mixture was extracted with ethyl acetate (20 mL*5), the collected layers were concentrated in vacuum to give a residue, and then re-dissolved in a solution of NaOH (19.06 g, 476.62 mmol, 1 eq) in Water (480 mL), followed by addition of ethyl acetate (50 mL). The aqueous solution was separated and washed with ethyl acetate (50 mL), acidified with 1 N HCl aqueous solution (5 mL), white solid precipitated, filtered to give a crude. The crude was used directly without further purification. 5-fluorobenzo[c][1,2]oxaborol-1(3H)-ol (42 g, 276.44 mmol, 58.00% yield) was obtained as a white solid.

Preparation of 3-chloro-8-fluoro-6H-isochromeno[3,4-d]pyrimidine (Compound 7 in FIG. 9)

A mixture of 5-fluorobenzo[c][1,2]oxaborol-1(3H)-ol (26.53 g, 174.63 mmol, 1.2 eq), 2,4-dichloro-5-iodo pyrimidine (40 g, 145.52 mmol, 1 eq), $Pd(dppf)Cl_2$ (10.65 g, 14.55 mmol, 0.1 eq), sodium carbonate (46.27 g, 436.56 mmol, 3 eq) in dioxane (400 mL) and Water (100 mL) was stirred at 80° C. for 2 h under nitrogen. The mixture was cooled to 20° C. and poured into a mixture of water (500 mL) and ethyl acetate (1000 mL), the aqueous solution was washed by ethyl acetate (1000 mL*2). The collected layers were washed with brine (500 mL), dried over anhydrous sodium sulfate, filtered and concentrated in vacuum to give a residue. The crude was triturated with dichloromethane (100 mL) at 20° C. for 30 min. 3-chloro-8-fluoro-6H-isochromeno[3,4-d]pyrimidine (25 g, 105.65 mmol, 72.60% yield) was obtained as an off-white solid.

Preparation of ARTX-413—8-fluoro-6H-isochromeno[3,4-d]pyrimidin-3-ol (FIG. 9)

To a solution of 3-chloro-8-fluoro-6H-isochromeno[3,4-d]pyrimidine (23 g, 97.20 mmol, 1 eq) in dioxane (600 mL) and Water (600 mL) was added potassium carbonate (24.18 g, 174.96 mmol, 1.8 eq) and 1,4-diazabicyclo[2.2.2]octane (5.45 g, 48.60 mmol, 5.34 mL, 0.5 eq) at 20° C., and the resulting mixture was stirred at 70° C. for 2 h. The mixture was cooled and acidified with 1 N HCl to pH=5 at 10° C., filtered and the filter-cake was collected. The crude was triturated with methanol (50 mL) at 25° ° C. for 1 h, then filtered to give a filter-cake. 8-fluoro-6H-isochromeno[3,4-d]pyrimidin-3-ol (11.38 g, 50.30 mmol, 51.75% yield, 96.403% purity) was obtained as an off-white solid.

Figure 10:
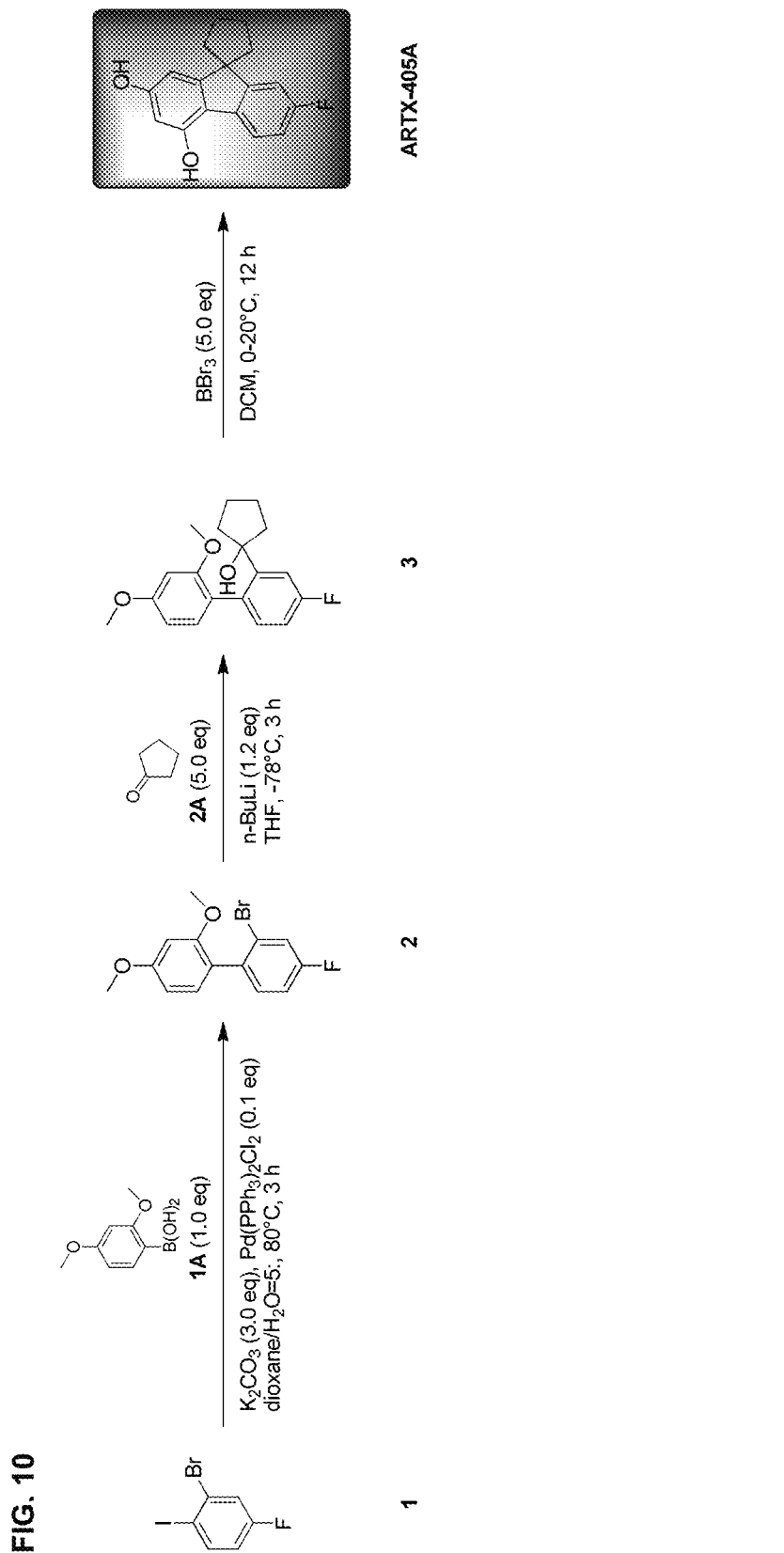
FIG. 10 shows a synthetic scheme for the synthesis of ARTX-405A.

A synthetic scheme for ARTX-405A is shown in FIG. 10.

Preparation of 2-bromo-4-fluoro-2',4'-dimethoxy-1,1'-biphenyl (Compound 2 in FIG. 10)

A mixture of 2-bromo-4-fluoro-1-iodo-benzene (25.0 g, 83.1 mmol, 1.00 eq), (2,4-dimethoxyphenyl)boronic acid (15.1 g, 83.1 mmol, 1.00 eq), potassium carbonate (34.5 g, 249.26 mmol, 3.00 eq), and bis(triphenylphosphine)palladium(II) chloride (5.83 g, 8.31 mmol, 0.100 eq) in dioxane (250 mL) and water (50.0 mL) was degassed and purged with nitrogen for 3 times, and then the mixture was stirred at 80° C. for 3 h under nitrogen atmosphere. The reaction mixture was diluted with water (1000 mL) and extracted with ethyl acetate (1000 mL×2). The combined organic layers were washed with brine (1000 mL), dried over anhydrous sodium sulfate, filtered and concentrated under reduced pressure to give a residue. The residue was purified by column chromatography ($SiO_2$, petroleum ether/ethyl acetate=0/1 to 20/1) to get 1-(2-bromo-4-fluoro-phenyl)-2,4-dimethoxy-benzene (48 g, 146.6 mmol, 88.2% yield, 95.0% purity) as a yellow solid.

Preparation of 1-(4-fluoro-2',4'-dimethoxy-[1,1'-biphenyl]-2-yl)cyclopentanol (Compound 3 in FIG. 10)

To a solution of 1-(2-bromo-4-fluoro-phenyl)-2,4-dimethoxy-benzene (12.0 g, 38.6 mmol, 1.00 eq) in tetrahydrofuran (200 mL) was added dropwise n-butyllithium (2.50 M, 18.5 mL, 1.20 eq) at −78° C. under nitrogen atmosphere. After addition, the mixture was stirred at this temperature for 1 h, and then cyclopentanone (9.73 g, 116 mmol, 10.2 mL, 3.00 eq) was added dropwise at −78° C. The resulting mixture was stirred at 20° C. for 2 h. The reaction mixture was quenched by addition of a saturated solution of ammonium chloride (100 mL) at 0° C., and then diluted with water (50.0 mL) and extracted with ethyl acetate (150 mL×3). The combined organic layers were washed with brine (200 mL), dried over anhydrous sodium sulfate, filtered and concentrated under reduced pressure to give a residue. The residue was purified by flash silica gel chromatography (ISCO®; 330 g SepaFlash® Silica Flash Column, Eluent of 0~20% ethyl acetate/petroleum ether gradient @ 100 ml/min) to get 1-[2-(2,4-dimethoxyphenyl)-5-fluoro-phenyl]cyclopentanol (16.0 g, 47.5 mmol, 30.8% yield, 94.0% purity) as a yellow oil.

Preparation of 7'-fluorospiro[cyclopentane-1,9'-fluorene]-2',4'-diol (ARTX-405A in FIG. 10)

To a solution of 1-[2-(2,4-dimethoxyphenyl)-5-fluorophenyl]cyclopentanol (8.00 g, 25.3 mmol, 1.00 eq) in dichloromethane (80.0 mL) was added boron tribromide (31.7 g, 126 mmol, 12.2 mL, 5.00 eq) at 0° C. The mixture was stirred at 25° C. for 12 h. The mixture was added dropwise to water (500 mL), the organic phase separated from the aqueous phase and extracted with dichloromethane (500×3 mL). The organic layers were combined and washed with brine (500 mL), dried over anhydrous sodium sulfate and concentrated to give a residue. The residue was purified by flash silica gel chromatography (ISCO®; 330 g SepaFlash® Silica Flash Column, Eluent of 0~20% ethyl acetate/petroleum ether gradient @ 100 mL/min) to get 7'-fluorospiro[cyclopentane-1,9'-fluorene]-2',4'-diol (10.32 g, 37.7 mmol, 74.5% yield, 98.7% purity) as an off-white solid.

Figure 11:
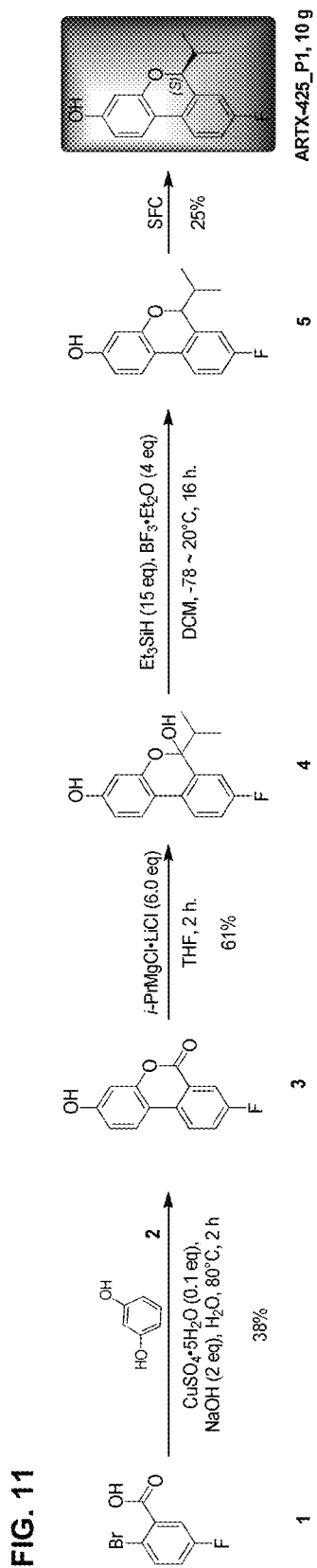
FIG. 11 shows a synthetic scheme for the synthesis of ARTX-425P1.

A synthetic scheme for ARTX-425-P1 is shown in FIG. 11.

Preparation of 8-fluoro-3-hydroxy-6H-benzo[c]chromen-6-one (Compound 3 in FIG. 11)

2-bromo-5-fluoro-benzoic acid (100 g, 456.60 mmol, 1 eq), resorcinol (100.55 g, 913.21 mmol, 152.35 mL, 2 eq), sodium hydroxide (36.53 g, 913.21 mmol, 2 eq) were dissolved in water (1 L), followed by addition of copper sulfate pentahydrate (11.40 g, 45.66 mmol, 0.1 eq). The mixture was stirred at 80° C. for 2 h under nitrogen. The mixture was filtered and the filter-cake was collected. The solid was mixed with methanol (100 mL) and then concentrated in vacuum to give a residue. The crude was used directly without further purification. 8-fluoro-3-hydroxy-6H-benzo[c]chromen-6-one (57.6 g, 248.73 mmol, 54.47% yield, 99.4% purity) was obtained as a red solid.

Preparation of 8-fluoro-6-isopropyl-6H-benzo[c]chromene-3,6-diol (Compound 4 in FIG. 11)

To a solution of 8-fluoro-3-hydroxy-6H-benzo[c]chromen-6-one (25 g, 108.61 mmol, 1 eq) in dry tetrahydrofuran (1.5 L) at −25° C. under nitrogen was added dropwise i-PrMgCl·LiCl (1.3 M, 501.26 mL, 6 eq). The mixture was stirred at −25° C. for 2 h and −10° C. for another 2 h. The reaction was quenched with sat. NH$_4$Cl (aq., 500 mL), diluted with water (500 mL) and extracted with ethyl acetate (2 L*3). The collected layers were washed with brine (1 L) and dried over anhydrous sodium sulfate, filtered and concentrated in vacuum to give a residue. The crude was used directly without further purification. 8-fluoro-6-isopropyl-6H-benzo[c]chromene-3,6-diol (40 g, 145.83 mmol, 67.14% yield) was obtained as a white solid.

Preparation of 8-fluoro-6-isopropyl-6H-benzo[c]chromen-3-ol (Compound 5 in FIG. 11)

To a solution of 8-fluoro-6-isopropyl-6H-benzo[c]chromene-3,6-diol (40 g, 145.83 mmol, 1 eq) in dichloromethane (1.6 L) was added Et$_3$SiH (254.36 g, 2.19 mol, 349.39 mL, 15 eq) and BF$_3$·Et$_2$O (82.79 g, 583.33 mmol, 71.99 mL, 4 eq) dropwise at −70° C., then the resulting mixture was stirred at 25° C. for further 16 h. The mixture was concentrated in vacuum to give a residue.

Preparation of ARTX-425 Peak 1 & ARTX-425_Peak 2—(S)-8-fluoro-6-isopropyl-6H-benzo[c]chromen-3-ol & (R)-8-fluoro-6-isopropyl-6H-benzo[c]chromen-3-ol (FIG. 11)

The crude was purified by prep-SFC (column: DAICEL CHIRALPAK AD (250 mm*50 mm, 10 um); mobile phase: [0.1% NH$_3$·H$_2$O EtOH]; B %: 45%-45%, B5.7; 150 min). (S)-8-fluoro-6-isopropyl-6H-benzo[c]chromen-3-ol (15.73 g, 60.58 mmol, 41.54% yield, 99.48% purity) was obtained as a white solid.

REFERENCES

1 Loftus, E. V., Jr. Update on the Incidence and Prevalence of Inflammatory Bowel Disease in the United States. *Gastroenterol Hepatol (NY)* 12, 704-707 (2016).

2 Buhner, S. et al. Genetic basis for increased intestinal permeability in families with Crohn's disease: role of CARD15 3020insC mutation? *Gut* 55, 342-347, doi: 10.1136/gut.2005.065557 (2006).

3 Gecse, K. et al. Leaky gut in patients with diarrhea-predominant irritable bowel syndrome and inactive ulcerative colitis. *Digestion* 85, 40-46, doi:10.1159/000333083 (2012).

4 Turpin, W. et al. Increased Intestinal Permeability Is Associated With Later Development of Crohn's Disease. *Gastroenterology* 159, 2092-2100 e2095, doi:10.1053/j.gastro.2020.08.005 (2020).

Wyatt, J., Vogelsang, H., Hubl, W., Waldhoer, T. & Lochs, H. Intestinal permeability and the prediction of relapse in Crohn's disease. *Lancet* 341, 1437-1439, doi:10.1016/0140-6736(93)90882-h (1993).

6 Clayburgh, D. R. et al. Epithelial myosin light chain kinase-dependent barrier dysfunction mediates T cell activation-induced diarrhea in vivo. *J Clin Invest* 115, 2702-2715, doi:10.1172/JCI24970 (2005).

7 D'Inca, R. et al. Intestinal permeability test as a predictor of clinical course in Crohn's disease. *Am J Gastroenterol* 94, 2956-2960, doi:10.1111/j.1572-0241.1999.01444.x (1999).

8 Odenwald, M. A. & Turner, J. R. Intestinal permeability defects: is it time to treat? *Clin Gastroenterol Hepatol* 11, 1075-1083, doi:10.1016/j.cgh.2013.07.001 (2013).

9 Su, L. et al. TNFR2 activates MLCK-dependent tight junction dysregulation to cause apoptosis-mediated barrier loss and experimental colitis. *Gastroenterology* 145, 407-415, doi:10.1053/j.gastro.2013.04.011 (2013).

10 Su, L. et al. Targeted epithelial tight junction dysfunction causes immune activation and contributes to development 11 Zuo, L., Kuo, W. T. & Turner, J. R. Tight Junctions as Targets and Effectors of Mucosal Immune Homeostasis. *Cell Mol Gastroenterol Hepatol* 10, 327-340, doi: 10.1016/j.jcmgh.2020.04.001 (2020).

12 Borody, T. J., Warren, E. F., Leis, S., Surace, R. & Ashman, O. Treatment of ulcerative colitis using fecal bacteriotherapy. *J Clin Gastroenterol* 37, 42-47, doi: 10.1097/00004836-200307000-00012 (2003).

13 Madsen, K. L. et al. Interleukin-10 gene-deficient mice develop a primary intestinal permeability defect in response to enteric microflora. *Inflamm Bowel Dis* 5, 262-270, doi:10.1097/00054725-199911000-00004 (1999).

14 Scheinin, T., Butler, D. M., Salway, F., Scallon, B. & Feldmann, M. Validation of the interleukin-10 knockout mouse model of colitis: antitumour necrosis factor-antibodies suppress the progression of colitis. *Clin Exp Immunol* 133, 38-43, doi:10.1046/j.1365-2249.2003.02193.x (2003).

15 Suenaert, P. et al. Anti-tumor necrosis factor treatment restores the gut barrier in Crohn's disease. *Am J Gastroenterol* 97, 2000-2004, doi:10.1111/j.1572-0241.2002.05914.x (2002).

16 Summers, R. W. et al. *Trichuris suis* seems to be safe and possibly effective in the treatment of inflammatory bowel disease. *Am J Gastroenterol* 98, 2034-2041, doi:10.1111/j.1572-0241.2003.07660.x (2003).

17 Graham, W. V. et al. Intracellular MLCK1 diversion reverses barrier loss to restore mucosal homeostasis. *Nat Med* 25, 690-700, doi:10.1038/s41591-019-0393-7 (2019).

18 Hollander, D. Crohn's disease—a permeability disorder of the tight junction? *Gut* 29, 1621-1624, doi:10.1136/gut.29.12.1621 (1988).

19 Konig, J. et al. Human Intestinal Barrier Function in Health and Disease. *Clin Transl Gastroenterol* 7, e196, doi:10.1038/ctg.2016.54 (2016).

20 Zeissig, S. et al. Changes in expression and distribution of claudin 2, 5 and 8 lead to discontinuous tight junctions and barrier dysfunction in active Crohn's disease. *Gut* 56, 61-72, doi:10.1136/gut.2006.094375 (2007).

21 Florholmen, J. Mucosal healing in the era of biologic agents in treatment of inflammatory bowel disease. *Scand J Gastroenterol* 50, 43-52, doi:10.3109/00365521.2014.977943 (2015).

22 Katsanos, K. H. & Papadakis, K. A. Inflammatory Bowel Disease: Updates on Molecular Targets for Biologics. *Gut Liver* 11, 455-463, doi:10.5009/gnl16308 (2017).

23 Tibble, J. A., Sigthorsson, G., Bridger, S., Fagerhol, M. K. & Bjarnason, I. Surrogate markers of intestinal inflammation are predictive of relapse in patients with inflammatory bowel disease. *Gastroenterology* 119, 15-22, doi: 10.1053/gast.2000.8523 (2000).

24 Arslan, G., Atasever, T., Cindoruk, M. & Yildirim, I. S. (51)CrEDTA colonic permeability and therapy response in patients with ulcerative colitis. *Nucl Med Commun* 22, 997-1001, doi:10.1097/00006231-200109000-00009 (2001).

25 Jenkins, R. T. et al. Small bowel and colonic permeability to 51Cr-EDTA in patients with active inflammatory bowel disease. *Clin Invest Med* 11, 151-155 (1988).

26 Teahon, K., Somasundaram, S., Smith, T., Menzies, I. & Bjarnason, I. Assessing the site of increased intestinal permeability in coeliac and inflammatory bowel disease. *Gut* 38, 864-869, doi:10.1136/gut.38.6.864 (1996).

27 Hollander, D. et al. Increased intestinal permeability in patients with Crohn's disease and their relatives. A possible etiologic factor. *Ann Intern Med* 105, 883-885, doi:10.7326/0003-4819-105-6-883 (1986).

28 Ma, C. et al. Innovations in Oral Therapies for Inflammatory Bowel Disease. *Drugs* 79, 1321-1335, doi: 10.1007/s40265-019-01169-y (2019).

29 Singh, S., Feuerstein, J. D., Binion, D. G. & Tremaine, W. J. AGA Technical Review on the Management of Mild-to-Moderate Ulcerative Colitis. *Gastroenterology* 156, 769-808 e729, doi:10.1053/j.gastro.2018.12.008 (2019).

30 Ham, M. & Moss, A. C. Mesalamine in the treatment and maintenance of remission of ulcerative colitis. *Expert Rev Clin Pharmacol* 5, 113-123, doi:10.1586/ecp.12.2 (2012).

31 Blonski, W., Buchner, A. M. & Lichtenstein, G. R. Inflammatory bowel disease therapy: current state-of-the-art. *Curr Opin Gastroenterol* 27, 346-357, doi:10.1097/MOG.0b013e328347aef3 (2011).

32 Sandborn, W. J. The Present and Future of Inflammatory Bowel Disease Treatment. *Gastroenterol Hepatol (NY)* 12, 438-441 (2016).

33 Ordas, I., Mould, D. R., Feagan, B. G. & Sandborn, W. J. Anti-TNF monoclonal antibodies in inflammatory bowel disease: pharmacokinetics-based dosing paradigms. *Clin Pharmacol Ther* 91, 635-646, doi:10.1038/clpt.2011.328 (2012).

34 Gaya, P., Peirotén, Á., Medina, M., Álvarez, I. & Landete, J. M. *Bifidobacterium pseudocatenulatum* INIA P815: The first bacterium able to produce urolithins A and B from ellagic acid. *Journal of Functional Foods* 45, 95-99, doi:https://doi.org/10.1016/j.jff.2018.03.040 (2018).

35 Dvorak, Z. et al. Weak Microbial Metabolites: a Treasure Trove for Using Biomimicry to Discover and Optimize Drugs. *Mol Pharmacol* 98, 343-349, doi:10.1124/molpharm.120.000035 (2020).

36 Cerda, B., Periago, P., Espin, J. C. & Tomas-Barberan, F. A. Identification of urolithin a as a metabolite produced by human colon microflora from ellagic acid and related compounds. *J Agric Food Chem* 53, 5571-5576, doi: 10.1021/jf050384i (2005).

37 Espin, J. C., Larrosa, M., Garcia-Conesa, M. T. & Tomas-Barberan, F. Biological significance of urolithins, the gut microbial ellagic Acid-derived metabolites: the evidence so far. *Evid Based Complement Alternat Med* 2013, 270418, doi:10.1155/2013/270418 (2013).

38 Fu, X. et al. Urolithin A targets the PI3K/Akt/NF-kappaB pathways and prevents IL-1beta-induced inflammatory response in human osteoarthritis: in vitro and in vivo studies. *Food Funct* 10, 6135-6146, doi:10.1039/c9fo01332f (2019).

39 Giménez-Bastida, J. A. et al. Ellagitannin metabolites, urolithin A glucuronide and its aglycone urolithin A, ameliorate TNF-α-induced inflammation and associated molecular markers in human aortic endothelial cells. *Molecular Nutrition & Food Research* 56, 784-796, doi: 10.1002/mnfr.201100677 (2012).

40 González-Sarrías, A., Larrosa, M., Tomás-Barberan, F. A., Dolara, P. & Espín, J. C. NF-κB-dependent anti-inflammatory activity of urolithins, gut microbiota ellagic acid-derived metabolites, in human colonic fibroblasts. *British Journal of Nutrition* 104, 503-512, doi:10.1017/S0007114510000826 (2010).

41 Komatsu, W., Kishi, H., Yagasaki, K. & Ohhira, S. Urolithin A attenuates pro-inflammatory mediator production by suppressing PI3-K/Akt/NF-kappaB and JNK/AP-1 signaling pathways in lipopolysaccharide-stimu- 41 lated RAW264 macrophages: Possible involvement of NADPH oxidase-derived reactive oxygen species. *Eur J Pharmacol* 833, 411-424, doi:10.1016/j.ejphar.2018.06.023 (2018).

42 Piwowarski, J. P., Kiss, A. K., Granica, S. & Moeslinger, T. Urolithins, gut microbiota-derived metabolites of ellagitannins, inhibit LPS-induced inflammation in RAW 264.7 murine macrophages. *Molecular Nutrition & Food Research* 59, 2168-2177, doi:10.1002/mnfr.201500264 (2015).

43 Wang, Y. et al. Role of TFEB in autophagic modulation of ischemia reperfusion injury in mice kidney and protection by urolithin A. *Food Chem Toxicol* 131, 110591, doi:10.1016/j.fct.2019.110591 (2019).

44 Singh, R. et al. Enhancement of the gut barrier integrity by a microbial metabolite through the Nrf2 pathway. *Nat Commun* 10, 89, doi:10.1038/s41467-018-07859-7 (2019).

45 Andreux, P. A. et al. The mitophagy activator urolithin A is safe and induces a molecular signature of improved mitochondrial and cellular health in humans. *Nature Metabolism* 1, 595-603, doi:10.1038/s42255-019-0073-4 (2019).

46 Baell, J. B. & Holloway, G. A. New substructure filters for removal of pan assay interference compounds (PAINS) from screening libraries and for their exclusion in bioassays. *J Med Chem* 53, 2719-2740, doi:10.1021/jm901137j (2010).

47 Hughes, T. B. & Swamidass, S. J. Deep Learning to Predict the Formation of Quinone Species in Drug Metabolism. *Chem Res Toxicol* 30, 642-656, doi:10.1021/acs.chemrestox.6b00385 (2017).

48 Limban, C. et al. The use of structural alerts to avoid the toxicity of pharmaceuticals. *Toxicol Rep* 5, 943-953, doi:10.1016/j.toxrep.2018.08.017 (2018).

49 Smith, G. F. Designing drugs to avoid toxicity. *Prog Med Chem* 50, 1-47, doi:10.1016/B978-0-12-381290-2.00001-X (2011).

50 Han, B. et al. Aryl Hydrocarbon Receptor Activation in Intestinal Obstruction Ameliorates Intestinal Barrier Dysfunction Via Suppression of MLCK-MLC Phosphorylation Pathway. *Shock* 46, 319-328, doi:10.1097/SHK.0000000000000594 (2016).

51 Scott, S. A., Fu, J. & Chang, P. V. Microbial tryptophan metabolites regulate gut barrier function via the aryl hydrocarbon receptor. *Proc Natl Acad Sci USA* 117, 19376-19387, doi:10.1073/pnas.2000047117 (2020).

52 Turner, J. R. Intestinal mucosal barrier function in health and disease. *Nat Rev Immunol* 9, 799-809, doi:10.1038/nri2653 (2009).

53 Lamas, B. et al. CARD9 impacts colitis by altering gut microbiota metabolism of tryptophan into aryl hydrocarbon receptor ligands. *Nat Med* 22, 598-605, doi:10.1038/nm.4102 (2016).

54 Li, Y. et al. Exogenous stimuli maintain intraepithelial lymphocytes via aryl hydrocarbon receptor activation. *Cell* 147, 629-640, doi:10.1016/j.cell.2011.09.025 (2011).

55 Kiss, E. A. et al. Natural aryl hydrocarbon receptor ligands control organogenesis of intestinal lymphoid follicles. *Science* 334, 1561-1565, doi:10.1126/science.1214914 (2011).

56 Qiu, J. et al. Group 3 innate lymphoid cells inhibit T-cell-mediated intestinal inflammation through aryl hydrocarbon receptor signaling and regulation of microflora. *Immunity* 39, 386-399, doi:10.1016/j.immuni.2013.08.002 (2013).

57 Qiu, J. et al. The aryl hydrocarbon receptor regulates gut immunity through modulation of innate lymphoid cells. *Immunity* 36, 92-104, doi:10.1016/j.immuni.2011.11.011 (2012).

58 Goettel, J. A. et al. AHR Activation Is Protective against Colitis Driven by T Cells in Humanized Mice. *Cell Rep* 17, 1318-1329, doi:10.1016/j.celrep.2016.09.082 (2016).

59 Monteleone, I. et al. Aryl hydrocarbon receptor-induced signals up-regulate IL-22 production and inhibit inflammation in the gastrointestinal tract. *Gastroenterology* 141, 237-248, 248 e231, doi:10.1053/j.gastro.2011.04.007 (2011).

60 Zelante, T. et al. Tryptophan catabolites from microbiota engage aryl hydrocarbon receptor and balance mucosal reactivity via interleukin-22. *Immunity* 39, 372-385, doi:10.1016/j.immuni.2013.08.003 (2013).

61 Islam, J. et al. Dietary tryptophan alleviates dextran sodium sulfate-induced colitis through aryl hydrocarbon receptor in mice. *J Nutr Biochem* 42, 43-50, doi:10.1016/j.jnutbio.2016.12.019 (2017).

62 Beischlag, T. V., Luis Morales, J., Hollingshead, B. D. & Perdew, G. H. The aryl hydrocarbon receptor complex and the control of gene expression. *Crit Rev Eukaryot Gene Expr* 18, 207-250, doi:10.1615/critreveukargeneexpr.v18.i3.20 (2008).

63 Loboda, A., Damulewicz, M., Pyza, E., Jozkowicz, A. & Dulak, J. Role of Nrf2/HO-1 system in development, oxidative stress response and diseases: an evolutionarily conserved mechanism. *Cell Mol Life Sci* 73, 3221-3247, doi:10.1007/s00018-016-2223-0 (2016).

64 Muku, G. E., Murray, I. A., Espín, J. C. & Perdew, G. H. Urolithin A Is a Dietary Microbiota-Derived Human Aryl Hydrocarbon Receptor Antagonist. *Metabolites* 8, 86, doi:10.3390/metabo8040086 (2018).

65 Dolciami, D. et al. Targeting Aryl hydrocarbon receptor for next-generation immunotherapies: Selective modulators (SAhRMs) versus rapidly metabolized ligands (RMAhRLs). *Eur J Med Chem* 185, 111842, doi:10.1016/j.ejmech.2019.111842 (2020).

66 Safe, S., Han, H., Goldsby, J., Mohankumar, K. & Chapkin, R. S. Aryl Hydrocarbon Receptor (AhR) Ligands as Selective AhR Modulators: Genomic Studies. *Curr Opin Toxicol* 11-12, 10-20, doi:10.1016/j.cotox.2018.11.005 (2018).

67 Safe, S., Jin, U. H., Park, H., Chapkin, R. S. & Jayaraman, A. Aryl Hydrocarbon Receptor (AHR) Ligands as Selective AHR Modulators (SAhRMs). *Int J Mol Sci* 21, doi:10.3390/ijms21186654 (2020).

68 Liu, J. Z. et al. Association analyses identify 38 susceptibility loci for inflammatory bowel disease and highlight shared genetic risk across populations. *Nat Genet* 47, 979-986, doi:10.1038/ng.3359 (2015).

69 McGovern, D. P. et al. Genome-wide association identifies multiple ulcerative colitis susceptibility loci. *Nat Genet* 42, 332-337, doi:10.1038/ng.549 (2010).

70 Antoniou, E. et al. The TNBS-induced colitis animal model: An overview. *Ann Med Surg (Lond)* 11, 9-15, doi:10.1016/j.amsu.2016.07.019 (2016).

71 Eichele, D. D. & Kharbanda, K. K. Dextran sodium sulfate colitis murine model: An indispensable tool for advancing our understanding of inflammatory bowel diseases pathogenesis. *World J Gastroenterol* 23, 6016-6029, doi:10.3748/wjg.v23.i33.6016 (2017).

72 Schneider, M. Dextran sodium sulfate-induced murine inflammatory colitis model. *Methods Mol Biol* 1031, 189-195, doi:10.1007/978-1-62703-481-4_21 (2013).

73 Cui, Y., Claus, S., Schnell, D., Runge, F. & MacLean, C. In-Depth Characterization of EpiIntestinal Microtissue as a Model for Intestinal Drug Absorption and Metabolism in Human. *Pharmaceutics* 12, doi:10.3390/pharmaceutics 12050405 (2020).

74 Petrulis, J. R., Chen, G., Benn, S., LaMarre, J. & Bunce, N. J. Application of the ethoxyresorufin-O-deethylase (EROD) assay to mixtures of halogenated aromatic compounds. *Environ Toxicol* 16, 177-184, doi:10.1002/tox.1022 (2001).

75 Cerda, B., Espin, J. C., Parra, S., Martinez, P. & Tomas-Barberan, F. A. The potent in vitro antioxidant ellagitannins from pomegranate juice are metabolised into bioavailable but poor antioxidant hydroxy-6H-dibenzopyran-6-one derivatives by the colonic microflora of healthy humans. *Eur J Nutr* 43, 205-220, doi:10.1007/s00394-004-0461-7 (2004).

76 Espin, J. C. et al. Iberian pig as a model to clarify obscure points in the bioavailability and metabolism of ellagitannins in humans. *J Agric Food Chem* 55, 10476-10485, doi:10.1021/jf0723864 (2007).

77 González-Sarrías, A. et al. Occurrence of urolithins, gut microbiota ellagic acid metabolites and proliferation markers expression response in the human prostate gland upon consumption of walnuts and pomegranate juice. *Molecular Nutrition & Food Research* 54, 311-322, doi: 10.1002/mnfr.200900152 (2010).

78 Heilman, J., Andreux, P., Tran, N., Rinsch, C. & Blanco-Bose, W. Safety assessment of Urolithin A, a metabolite produced by the human gut microbiota upon dietary intake of plant derived ellagitannins and ellagic acid. *Food Chem Toxicol* 108, 289-297, doi:10.1016/j.fct.2017.07.050 (2017).

79 Larrosa, M. et al. Anti-inflammatory properties of a pomegranate extract and its metabolite urolithin-A in a colitis rat model and the effect of colon inflammation on phenolic metabolism. *The Journal of Nutritional Biochemistry* 21, 717-725, doi:https://doi.org/10.1016/j.jnutbio.2009.04.012 (2010).

80 Seeram, N. P. et al. Pomegranate juice ellagitannin metabolites are present in human plasma and some persist in urine for up to 48 hours. *J Nutr* 136, 2481-2485, doi:10.1093/jn/136.10.2481 (2006).

81 Tomas-Barberan, F. A. et al. Urolithins, the rescue of "old" metabolites to understand a "new" concept: Metabotypes as a nexus among phenolic metabolism, microbiota dysbiosis, and host health status. *Mol Nutr Food Res* 61, doi:10.1002/mnfr.201500901 (2017).

82 Singh, A. et al. Direct supplementation with Urolithin A overcomes limitations of dietary exposure and gut microbiome variability in healthy adults to achieve consistent levels across the population. *Eur J Clin Nutr*, doi: 10.1038/s41430-021-00950-1 (2021).

What is claimed is:

1. A compound of Formula (I)

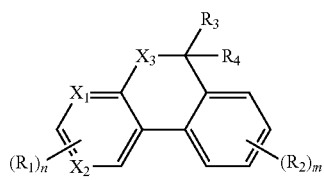

(I)

or a pharmaceutically acceptable salt or solvate thereof, wherein:

each $R_1$ is independently selected from the group consisting of OH, $NO_2$, Halo, $CF_3$, $NR_3R_4$, $(C_1-C_6)$ alkoxy, —C(O)$(C_1-C_6)$ alkyl, and —C(O)O$(C_1-C_6)$ alkyl;

each $R_2$ is a substituent other than OH;

$R_3$ and $R_4$ each is independently selected from the group consisting of H, alkyl, alkenyl, alkoxy, cycloalkyl, heterocyclo, aryl, heteroaryl, and $R_3$ and $R_4$ together with the carbon to which they are attached form a $(C_3-C_8)$ cycloalkyl or $(C_3-C_8)$ heterocyclo;

$X_1$ and $X_2$ are each independently C or N, with proviso that $X_1$ and $X_2$ cannot be both C;

$X_3$ is O or S;

m is an integer in the range of 1 to 4; and n is an integer in the range of 1 to 4, wherein $R_2$ is Halo and m is 1 or 2; or wherein $X_1$ and $X_2$ are each N.

2. The compound of claim 1, wherein $R_1$ is OH, and n is 1 or 2.

3. The compound of claim 2, wherein n is 1.

4. The compound of claim 1, wherein $R_2$ is Halo, and m is 1 or 2.

5. The compound of claim 4, wherein m is 1.

6. The compound of claim 4, wherein $R_2$ is F.

7. The compound of claim 1, wherein $X_1$ and $X_2$ are each N.

8. The compound of claim 1, wherein $X_3$ is O.

9. The compound of claim 1, wherein $R_3$ and $R_4$ are each H.

10. The compound of claim 1, wherein one of $R_3$ and $R_4$ is $(C_1-C_6)$ alkyl or $(C_2-C_6)$ alkenyl, and the other is H.

11. The compound of claim 1, wherein $R_3$ and $R_4$ together with the carbon to which they are attached form a $(C_3-C_8)$ cycloalkyl or $(C_3-C_8)$ heterocyclo.

12. The compound of claim 1, wherein:

$R_1$ is OH and n is 1;

$R_2$ is Halo and m is 1;

$X_1$ and $X_2$ are both N;

$X_3$ is O; and $R_3$ and $R_4$ are each H.

13. The compound of claim 12, wherein $R_2$ is F.

14. The compound of claim 13, having the structure:

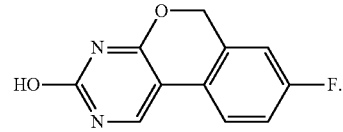 [SMILES: Oc1ncc2c(n1)OCc1cc(F)ccc1-2]

15. The compound of claim 1, wherein:

$R_1$ is OH and n is 1;

$R_2$ is F and m is 1;

$X_1$ and $X_2$ are both N;

$X_3$ is O;

$R_3$ is H; and $R_4$ is isopropyl.

16. A pharmaceutical composition comprising the compound of claim 1 or a pharmaceutically acceptable salt or solvate thereof, and a pharmaceutically acceptable excipient and/or carrier.

17. The pharmaceutical composition of claim 16, wherein the composition is formulated for oral delivery to the gastrointestinal tract.

18. The pharmaceutical composition of claim 17, wherein the composition is formulated for delivery to the small intestine and/or the large intestine.

19. A method of treating an epithelial disorder of the gastrointestinal tract in a subject, the method comprising administering to the subject the pharmaceutical composition of claim 16, wherein the epithelial disorder is selected from inflammatory bowel disease, irritable bowel syndrome, ulcerative colitis, Crohn's disease, radiation-induced mucositis or intestinal permeability, and drug-induced mucositis or intestinal permeability.

20. The method of claim 19, wherein the disorder is inflammatory bowel disease or irritable bowel syndrome.

21. The method of claim 20, wherein the inflammatory bowel disease is ulcerative colitis or Crohn's disease.

22. The method of claim 19, wherein the disorder is celiac disease.

23. The method of claim 19, wherein the disorder is radiation-induced mucositis or intestinal permeability, or drug-induced mucositis or intestinal permeability.

* * * * *